United States Patent
Bogatkevich et al.

(10) Patent No.: US 10,344,071 B2
(45) Date of Patent: Jul. 9, 2019

(54) IDENTIFICATION OF NOVEL ANTI-FIBROTIC PEPTIDE IN C-TERMINAL REGION OF THE MET RECEPTOR TYROSINE KINASE

(71) Applicant: MUSC Foundation for Research Development, Charleston, SC (US)

(72) Inventors: Galina S. Bogatkevich, Mt. Pleasant, SC (US); Yuichiro Shirai, Charleston, SC (US); Richard M. Silver, Charleston, SC (US)

(73) Assignee: MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 0 days.

(21) Appl. No.: 15/747,805

(22) PCT Filed: Jul. 21, 2016

(86) PCT No.: PCT/US2016/043376
§ 371 (c)(1),
(2) Date: Jan. 26, 2018

(87) PCT Pub. No.: WO2017/019454
PCT Pub. Date: Feb. 2, 2017

(65) Prior Publication Data
US 2018/0215802 A1 Aug. 2, 2018

Related U.S. Application Data

(60) Provisional application No. 62/197,923, filed on Jul. 28, 2015.

(51) Int. Cl.
| | | |
|---|---|---|
| *C07K 14/705* | (2006.01) | |
| *A61K 45/06* | (2006.01) | |
| *C07K 14/71* | (2006.01) | |
| *A61P 17/00* | (2006.01) | |
| *A61K 38/17* | (2006.01) | |
| *A61K 38/00* | (2006.01) | |

(52) U.S. Cl.
CPC .......... *C07K 14/705* (2013.01); *A61K 38/177* (2013.01); *A61K 45/06* (2013.01); *A61P 17/00* (2018.01); *C07K 14/71* (2013.01); *A61K 38/00* (2013.01); *C07K 2319/50* (2013.01)

(58) Field of Classification Search
None
See application file for complete search history.

(56) References Cited

U.S. PATENT DOCUMENTS

| | | |
|---|---|---|
| 8,865,673 B2 | 10/2014 | Detmar |
| 2005/0113284 A1 | 5/2005 | Nakamura |
| 2010/0305156 A1 | 12/2010 | Lauffer |
| 2011/0012894 A1 | 1/2011 | Wiesmann |
| 2012/0263723 A1 | 10/2012 | Davies |
| 2013/0274215 A1 | 10/2013 | Thies |

OTHER PUBLICATIONS

Shirai, Yuichiro et al, "Anti-fibrotic effects of a newly discovered hgf receptor carboxyl terminal fragment in systemic sclerosis." 2014 ACR/ARHP annual meeting, abstract 3002, available Oct. 2014.*

Atanelishvili, Ilia et al, "M10, a caspase cleavage product of the hepatocyte growth factor receptor, interacts with smad2 and demonstrates antifibrotic properties in vitro and in vivo." Trans. Res. (2106) 170 p. 99-111.*

Manno, Rebecca and Boin, Francesco, "Immunotherapy of systemic sclerosis." Immunother. (2010) 2(6) p. 863-878.*

S. Dennler, S. Itoh, D. Vivien, P. ten Dijke, S. Huet, J.-M. Gauthier. Direct binding of Smad3 and Smad4 to critical TGFβ-inducible elements in the promoter of human plasminogen activator inhibitor-type 1 gene. EMBO J., 1998;17:3091-3100.

Han G, Li AG, Liang YY, Owens P, He W, Lu S, Yoshimatsu Y, Wang D, Ten Dijke P, Lin X, Wang XJ. Smad7-induced beta-catenin degradation alters epidermal appendage development. Dev Cell. 2006;11(3):301-12.

Harvey KA, Paranavitana CN, Zaloga GP, Siddiqui RA. Diverse signaling pathways regulate fibroblast differentiation and transformation through Rho kinase activation. J Cell Physiol. 2007;211(2):353-63.

Bogatkevich GS, Ludwicka-Bradley A, Nietert PJ, Alder T, van Ryn J, Silver RM. Anti-inflammatory and anti-fibrotic effects of the oral direct thrombin inhibitor dabigatran etexilate in a murine model of interstitial lung disease. Arthritis Rheum. 2011;63(5):1416-25.

Luzina IG, Kopach P, Lockatell V. Kang PH, Nagarsekar A, Burke AP, Hasday JD, Todd NW, Atamas SP. Interleukin-33 potentiates bleomycin-induced lung injury. Am J Respir Cell Mol Biol. 2013;49(6):999-1008.

Lee CG, Herzog EL, Ahangari F, Zhou Y, Gulati M, Lee CM, Peng X, Feghali-Bostwick C, Jimenez SA, Varga J, Elias JA. Chitinase 1 is a biomarker for and therapeutic target in scleroderma-associated interstitial lung disease that augments TGF-β1 signaling. J Immunol. 2012;189(5):2635-44.

Moeller A, Ask K, Warburton D, Gauldie J, Kolb M. The bleomycin animal model: a useful tool to investigate treatment options for idiopathic pulmonary fibrosis? Int J Biochem Cell Biol. 2008;40(3):362-82.

(Continued)

*Primary Examiner* — Fred H Reynolds
(74) *Attorney, Agent, or Firm* — Riverside Law LLP

(57) ABSTRACT

The invention provides anti-fibrotic peptides derived from the C-terminal region of the MET receptor tyrosine kinase. Polynucleotides encoding these peptides, host cells transformed with the polynucleotides, and methods of using these peptides and polynucleotides are included in the invention. Uses of these peptides, polynucleotides and expression vectors include the treatment of fibrosis in a subject.

15 Claims, 18 Drawing Sheets
Specification includes a Sequence Listing.

(56) References Cited

OTHER PUBLICATIONS

Wu M, Varga J. In perspective: murine models of scleroderma. Curr Rheumatol Rep. 2008;10(3):173-82.

Crestani, Bruno, et al. "Hepatocyte growth factor and lung fibrosis." Proceedings of the American Thoracic Society 9.3 (2012): 158-163.

Kieffer I; Song J; Lukas D; Hasan M; Neumann B; Croxford AL; Pedre X; Hovelmeyer N; Yogev N; Mildner A; Prinz M; Wiese E; Reifenberg K; Bittner S; Wiendl H; Steinman L; Becker C; Bogdahn U; Neurath MF; Steinbrecher A; Waisman A. 2010. Smad7 in T cells drives T helper 1 responses in multiple sclerosis and experimental autoimmune encephalomyelitis. Brain 133(Pt 4)1067-81.

Zheng B; Zhang Z; Black CM; de Crombrugghe B; Denton CP. 2002. Ligand-dependent genetic recombination in fibroblasts : a potentially powerful technique for investigating gene function in fibrosis. Am J Pathol 160(5):1609-17.

Chung MP, Monick MM, Hamzeh NY, Butler NS, Powers LS, Hunninghake GW. Role of repeated lung injury and genetic background in bleomycin-induced fibrosis. Am J Respir Cell Mol Biol. 2003;29(3 Pt 1):375-80.

Degryse AL, Tanjore H, Xu XC, Polosukhin VV, Jones BR, McMahon FB, Gleaves LA, Blackwell TS, Lawson WE. Repetitive intratracheal bleomycin models several features of idiopathic pulmonary fibrosis. Am J Physiol Lung Cell Mol Physiol. 2010;299(4):L442-52.

Lin, Yong, et al. "Treatment of experimental hepatic fibrosis by combinational delivery of urokinase-type plasminogen activator and hepatocyte growth factor genes." Liver International 25A (2005): 796-807.

Kajihara, Ikko, et al. "Overexpression of hepatocyte growth factor receptor in scleroderma dermal fibroblasts is caused by autocrine transforming growth factor β signaling." Bioscience trends 6.3 (2012): 136-142.

Barkauskas, Christina E., and Paul W. Noble. "Cellular mechanisms of tissue fibrosis. 7. New insights into the cellular mechanisms of pulmonary fibrosis." American Journal of Physiology-Cell Physiology 306.11 (2014): C987-C996.

Hardie, William D., Stephan W. Glasser, and James S. Hagood. "Emerging concepts in the pathogenesis of lung fibrosis." The American journal of pathology 175.1 (2009): 3-16.

Zoz, Donald F., William E. Lawson, and Timothy S. Blackwell. "Idiopathic pulmonary fibrosis: a disorder of epithelial cell dysfunction." The American journal of the medical sciences 341.6 (2011): 435-438.

Ashcroft, T., Judy M. Simpson, and V. Timbrell. "Simple method of estimating severity of pulmonary fibrosis on a numerical scale." Journal of clinical pathology 41.4 (1988): 467-470.

Gazdhar, Amiq, et al. "Targeted gene transfer of hepatocyte growth factor to alveolar type II epithelial cells reduces lung fibrosis in rats." Human gene therapy 24.1 (2012): 105-116.

Van Den Hoogen, Frank, et al. "2013 classification criteria for systemic sclerosis: an American College of Rheumatology/European League against Rheumatism collaborative initiative." Arthritis & Rheumatism 65.11 (2013): 2737-2747.

Vlieghe, Patrick, et al. "Synthetic therapeutic peptides: science and market." Drug discovery today 151.2 (2010): 40-56.

Wynn, T. A. "Cellular and molecular mechanisms of fibrosis." The Journal of Pathology: A Journal of the Pathological Society of Great Britain and Ireland 214.2 (2008): 199-210.

Fan, Ming-Hui, Carol A. Feghali-Bostwick, and Richard M. Silver. "Update on scleroderma-associated interstitial lung disease." Current opinion in rheumatology 26.6 (2014): 630.

Bogatkevich, G. S. "Lung involvement in scleroderma." Rheumatol Curr Res 1 (2012): e001.

Ishida, Wataru, et al. "Intracellular TGF-β receptor blockade abrogates Smad-dependent fibroblast activation in vitro and in vivo." Journal of Investigative Dermatology 126.8 (2006): 1733-1744.

Chacko, Benoy M., et al. "Structural basis of heteromeric Smad protein assembly in TGF-β signaling." Molecular cell 15.5 (2004): 813-823.

Hill, Caroline S. "The smads." The international journal of biochemistry & cell biology 31.11 (1999): 1249-1254.

Varga, John, and Michael L. Whitfield. "Transforming growth factor-beta in systemic sclerosis (scleroderma)." Front Eliosci (Schol Ed) 1.1 (2009): 226-235.

Mizuno S, Matsumoto K, Li MY, Nakamura T. HGF reduces advancing lung fibrosis in mice: a potential role for MMP-dependent myofibroblast apoptosis. FASEB J 2005; 19:580-2.

Suzumura K, Hirano T, Son G, Iimuro Y, Mizukami H, Ozawa K, Fujimoto J. Adeno-associated virus vector-mediated production of hepatocyte growth factor attenuates liver fibrosis in mice. Hepatol Int. 2008; 2:80-8.

Dai C, Liu Y. Hepatocyte growth factor antagonizes the profibrotic action of TGF-β in mesangial cells by stabilizing Smad transcriptional corepressor TGIF. J Am Soc Nephrol 2004; 15:1402-1412.

Bogatkevich GS, Ludwicka-Bradley A, Highland KB, Hant F, Nietert PJ, Singleton CB, Feghali-Bostwick CA, Silver RM. Impairment of the Antifibrotic Effect of Hepatocyte Growth Factor in Lung Fibroblasts from African-Americans. Possible Role in Systemic Sclerosis. Arthritis Rheum 2007; 56:2432-42.

Bogatkevich GS, Ludwicka-Bradley A, Highland KB, Hant F, Nietert PJ, Singleton CB, Silver RM. Down-regulation of caollagen and connective tissue growth factor expression with hepatocyte growth factor in lung fibroblasts from white scleroderma patients via two signaling pathways. Arthritis Rheum 2007; 56:3468-77.

Ataneliveshili I, Akter T, Silver RM, Bogatkevich GS. D1398G Variant of Hepatocyte Growth Factor Receptor—A Potential Biomarker of Severe Interstitial Lung Disease in African American Scleroderma Patients. Arthritis Rheum. 2013; 65(10 Suppl.), 2907.

D'Angelo WA, Fries JF, Masi AT, Shulman LE. Pathologic observations in systemic sclerosis (scleroderma). A study of fifty-eight autopsy cases and fifty-eight matched controls. Am J Med. 1969; 46(3):428-40.

Steen VD, Medsger TA. Changes in causes of death in systemic sclerosis, 1972-2002. Ann Rheum Dis. 2007; 66(7):940-4.

Nietert PJ, Mitchell HC, Bolster MB, Shaftman SR, Tilley BC, Silver RM. Racial variation in clinical and immunological manifestations of systemic sclerosis. J Rheumatol 2006; 33:263-268.

Silver RM, Bogatkevich GS, Tourkina E, Nietert PJ, Hoffman S. Racial differences between blacks and whites with systemic sclerosis. Curr Opin Rheumatol. 2012;24(6):642-8.

Ohmichi H, Koshimizu U, Matsumoto K, Nakamura T. Hepatocyte growth factor (HGF) acts as a mesenchyme-derived morphogenic factor during fetal lung development. Development 1998; 125(7):1315-24.

Neuss S, Becher E, Wöltje M, Tietze L, Jahnen-Dechent W. Functional expression of HGF and HGF receptor/c-met in adult human mesenchymal stem cells suggests a role in cell mobilization, tissue repair, and wound healing. Stem Cells 2004; 22:405-14.

Stuart KA, Riordan SM, Lidder S, Crostella L, Williams R, Skouteris GG. Hepatocyte growth factor/scatter factor-induced intracellular signaling. Int J Exp Pathol 2000; 81:17-30.

Hammond DE, Carter S, Clague MJ. Met receptor dynamics and signaling. Curr Top Microbiol Immunol 2004; 286:21-44.

Jinnin M, Inn H, Mimura Y, Asano Y, Yamane K, Tamaki K. Effects of hepatocyte growth factor on the expression of type I collagen and matrix metalloproteinase-1 on normal and scleroderma dermal fibroblasts. J Invest Dermatol 2005;124:324-30.

Sherriff-Tadano R, Ohta A, Morito F et al. Antifibrotic effects of hepatocyte growth factor on scleroderma fibroblasts and analysis of its mechanism. Mod Rheumatol 2006;16:364-71.

Trabuco LG, Lise S, Petsalaki E, Russell RB. PepSite:prediction of peptide-binding sites from protein surfaces. Nucleic Acids Res. 2012; 40(Web Server issue):W423-7.

Wang H, Yang YF, Zhao L, Xiao FJ, Zhang QW, Wen ML, Wu CT, Peng RY, Wang LS. Hepatocyte growth factor gene-modified mesenchymal stem cells reduce radiation-induced lung injury. Hum Gene Ther. 2013;24(3):343-53.

Marquardt Ju, Seo D, Gómez-Quiroz LE, Uchida K, Gillen MC, Kitade M, Kaposi-Novak P, Conner EA, Factor VM, Thorgeirsson SS. Loss of c-Met accelerates development of liver fibrosis in response to CCl(4) exposure through deregulation of multiple molecular pathways. Biochim Biophys Acta. 2012;1822(6):942-51.

(56) References Cited

OTHER PUBLICATIONS

Giebeler A, Boekschoten MV, Klein C, Borowiak M, Birchmeier C, Gassier N, Wasmuth HE, Müller M, Trautwein C, Streetz KL. c-Met confers protection against chronic liver tissue damage and fibrosis progression after bile duct ligation in mice. Gastroenterology. 2009;137(1):297-308.

Goetsch L, Caussanel V, Corvaia N. Biological significance and targeting of c-Met tyrosine kinase receptor in cancer. Front Biosci (Landmark Ed). 2013;18:454-73.

Trusolino L, Bertotti A, Comoglio PM. MET signalling: principles and functions in development, organ regeneration and cancer Nat Rev Mol Cell Biol. 2010 D;11(12):834-48.

Tulasne D, Deheuninck J, Lourenco FC, Lamballe F, Ji Z, Leroy C, Puchois E, Moumen A, Maina F, Mehlen P, Fafeur V. Proapoptotic function of the MET tyrosine kinase receptor through caspase cleavage. Mol Cell Biol. 2004;24(23):10328-39.

Foveau B, Leroy C, Ancot F, Deheuninck J, Ji Z, Fafeur V, Tulasne D. Amplification of apoptosis through sequential caspase cleavage of the MET tyrosine kinase receptor. Cell Death Differ. 2007;14(4):752-64.

Lefebvre J, Muharram G, Leroy C, Kherrouche Z, Montagne R, Ichim G, Tauszig-Delamasure S, Chotteau-Lelievre A, Brenner C, Mehlen P, Tulasne D. Caspase-generated fragment of the Met receptor favors apoptosis via the intrinsic pathway independently of its tyrosine kinase activity. Cell Death Dis. Oct. 17, 2013;4:e871. doi: 10.1038/cddis.2013.377.

Ma J, Zou C, Guo L, Seneviratne DS, Tan X, Kwon YK, An J, Bowser R, Defrances MC, Zamegar R. A novel death defying domain in met entraps the active site of caspase-3 and blocks apoptosis in hepatocytes. Hepatology. Oct. 3, 2013. doi: 10.1002/hep.26769.

Fonseca SB, Pereira MP, Kelley SO. Recent advances in the use of cell-penetrating peptides for medical and biological applications. Adv Drug Deliv Rev. 2009;61(11):953-64.

Kawaguchi Y, Harigai M, Hara M, Fukasawa C, Takagi K, Tanaka M, Tanaka E, Nishimagi E, Kamatani N. Expression of hepatocyte growth factor and its receptor (c-met) in skin fibroblasts from patients with systemic sclerosis. J Rheumatol 2002;29:1877-83.

Tokunou M, Niki T, Eguchi K, Iba S, Tsuda H, Yamada T, Matsuno Y, Kondo H, Saitoh Y, Imamura H, Hirohashi S. c-MET expression in myofibroblasts : role in autocrine activation and prognostic significance in lung adenocarcinoma. Am. J. Pathol 2001;158:1451-63.

Kim WH, Matsumoto K, Bessho K, Nakamura T. Growth inhibition and apoptosis in liver myofibroblasts promoted by hepatocyte growth factor leads to resolution from liver cirrhosis. Am J Pathol 2005;166(4):1017-28.

Bogatkevich, Galina S., et al. "Thrombin differentiates normal lung fibroblasts to a myofibroblast phenotype via the proteolytically activated receptor-1 and a protein kinase C-dependent pathway." Journal of Biological Chemistry 276.48(2001): 45184-45192.

Slee EA, Adrain C, Martin SJ. Executioner caspase-3, -6, and -7 perform distinct, non-redundant roles during the demolition phase of apoptosis. J Biol Chem. 2001;276(10):7320-6.

Woo M, Hakem R, Furlonger C, Hakem A, Duncan GS, Sasaki T, Bouchard D, Lu L, Wu GE, Paige CJ, Mak TW. Caspase-3 regulates cell cycle in B cells: a consequence of substrate specificity. Nat Immunol. 2003;4(10):1016-22.

De Botton S, Sabri S, Daugas E, Zermati Y, Guidotti JE, Hermine O, Kroemer G, Vainchenker W, Debili N. Platelet formation is the consequence of caspase activation within megakaryocytes. Blood. 2002;100(4):1310-7.

Okazaki S, Ogawa F, Iwata Y, Hara T, Muroi E, Komura K, Takenaka M, Shimizu K, Hasegawa M, Fujimoto M, Sato S. Autoantibody against caspase-3, an executioner of apoptosis, in patients with systemic sclerosis. Rheumatol Int. 2010;30(7):871-8.

Bogatkevich GS, Gustilo E, Oates JC, Feghali-Bostwick C, Harley RA, Silver RM, Ludwicka-Bradley A. Distinct PKC isoforms mediate cell survival and DNA synthesis in thrombin-induced myofibroblasts. Am J Physiol Lung Cell Mol Physiol. 2005;288:L190-201.

Yan X, Liu Z, Chen Y. Regulation of TGF-β signaling by Smad7. Acta Biochim Biophys Sin. 2009;41(4):263-72.

Briones-Orta MA, Tecalco-Cruz AC, Sosa-Garrocho M, Caligaris C, Macias-Silva M. Inhibitory Smad7: emerging roles in health and disease. Curr Mol Pharmacol. 2011;4(2):141-53.

Hayashi H, Abdollah S, Qiu Y, Cai J, Xu YY, Grinnell BW, Richardson MA, Topper JN, Gimbrone MA Jr, Wrana JL, Falb D. The MAD-related protein Smad7 associates with the TGFβ receptor and functions as an antagonist of TGFbeta signaling. Cell. 1997;89(7)1165-73.

Kopp J, Preis E, Said H, Hafemann B, Wickert L, Gressner AM, Pallua N, Dooley S. Abrogation of transforming growth factor-beta signaling by SMAD7 inhibits collagen gel contraction of human dermal fibroblasts. J Biol Chem. 2005;280(22):21570-6.

Kavsak P, Rasmussen RK, Causing CG, Bonni S, Zhu H, Thomsen GH, Wrana JL. Smad7 binds to Smurf2 to form an E3 ubiquitin ligase that targets the TGFβ receptor for degradation. Mol Cell. 2000;6(6):1365-75.

Ebisawa T, Fukuchi M, Murakami G, Chiba T, Tanaka K, Imamura T, Miyazono K. Smurf1 interacts with transforming growth factor-beta type I receptor through Smad7 and induces receptor degradation. J Biol Chem. 2001;276(16):12477-80.

Zhang S, Fei T, Zhang L, Zhang R, Chen F, Ning Y, Han Y, Feng XH, Meng A, Chen YG. Smad7 antagonizes transforming growth factor beta signaling in the nucleus by interfering with functional Smad-DNA complex formation. Mol Cell Biol. 2007;27(12):4488-99.

I Atanelishvili, J Liang, T Akter, D. D. Spyropoulos, RM Silver and GS Bogatkevich. Thrombin increases lung fibroblast survival while promoting alveolar epithelial cell apoptosis via the ER stress marker CHOP. Am J Respir Cell Mol Biol. Nov. 26, 2013.

Bogatkevich GS, Ludwicka-Bradley A, Silver RM. Dabigatran, a direct thrombin inhibitor, demonstrates anti-fibrotic effects on lung fibroblasts. Arthritis Rheum. 2009;60(11):3455-3464.

Verrecchia F, Mauviel A, Farge D. Transforming growth factor-beta signaling through the Smad proteins: role in systemic sclerosis. Autoimmun Rev. 2006;5(8):563-9.

Bartram U, Speer CP. The role of transforming growth factor beta in lung development and disease. Chest. 2004;125(2):754-65.

Chen SJ, Yuan W, Mod Y, Levenson A, Trojanowska M, Varga J. Stimulation of type I collagen transcription in human skin fibroblasts by TGF-beta: involvement of Smad 3. J Invest Dermatol. 1999;112(1):49-57.

Evans RA, Tian YC, Steadman R, Phillips AO. TGF-beta1-mediated fibroblast-myofibroblast terminal differentiation-the role of Smad proteins. Exp Cell Res. 2003;282(2):90-100.

Liu X, Sun Y, Constantinescu SN, Karam E, Weinberg RA, Lodish HF. Transforming growth factor beta-induced phosphorylation of Smad3 is required for growth inhibition and transcriptional induction in epithelial cells. Proc Natl Acad Sci U S A. 1997;94(20):10669-74.

* cited by examiner

SEQUENCE LISTING

```
<160> NUMBER OF SEQ ID NOS: 9

<210> SEQ ID NO 1
<211> LENGTH: 10
<212> TYPE: PRT
<213> ORGANISM: Artificial Sequence
<220> FEATURE:
<223> OTHER INFORMATION: M10 Peptide

<400> SEQUENCE: 1

Thr Arg Pro Ala Ser Phe Trp Glu Thr Ser
1               5                   10

<210> SEQ ID NO 2
<211> LENGTH: 9
<212> TYPE: PRT
<213> ORGANISM: Artificial Sequence
<220> FEATURE:
<223> OTHER INFORMATION: 1404 Peptide

<400> SEQUENCE: 2

Asp Glu Val Asp Thr Arg Pro Ala Ser
1               5

<210> SEQ ID NO 3
<211> LENGTH: 10
<212> TYPE: PRT
<213> ORGANISM: Artificial Sequence
<220> FEATURE:
<223> OTHER INFORMATION: 1403 Peptide

<400> SEQUENCE: 3

Asp Asp Glu Val Asp Thr Arg Pro Ala Ser
1               5                   10

<210> SEQ ID NO 4
<211> LENGTH: 5
<212> TYPE: PRT
<213> ORGANISM: Artificial Sequence
<220> FEATURE:
<223> OTHER INFORMATION: M5 Peptide

<400> SEQUENCE: 4

Thr Arg Pro Ala Ser
1               5
```

```
<210> SEQ ID NO 5
<211> LENGTH: 19
<212> TYPE: PRT
<213> ORGANISM: Artificial Sequence
<220> FEATURE:
<223> OTHER INFORMATION: MET C-terminal seuqence

<400> SEQUENCE: 5

Glu Asp Asn Ala Asp Asp Glu Val Asp Thr Arg Pro Ala Ser Phe Trp
1               5                   10                  15

Glu Thr Ser

<210> SEQ ID NO 6
<211> LENGTH: 14
<212> TYPE: PRT
<213> ORGANISM: Artificial Sequence
<220> FEATURE:
<223> OTHER INFORMATION: M10 with caspase cleavage site

<400> SEQUENCE: 6

Asp Glu Val Asp Thr Arg Pro Ala Ser Phe Trp Glu Thr Ser
1               5                   10

<210> SEQ ID NO 7
<211> LENGTH: 15
<212> TYPE: PRT
<213> ORGANISM: Artificial Sequence
<220> FEATURE:
<223> OTHER INFORMATION: M10 with caspase cleavage site and N-terminal
      aspartate

<400> SEQUENCE: 7

Asp Asp Glu Val Asp Thr Arg Pro Ala Ser Phe Trp Glu Thr Ser
1               5                   10                  15

<210> SEQ ID NO 8
<211> LENGTH: 37
<212> TYPE: DNA
<213> ORGANISM: Artificial Sequence
<220> FEATURE:
<223> OTHER INFORMATION: Forward MET primer

<400> SEQUENCE: 8
gaagataacg ctgatgatga ggtgggcaca cgaccag                            37

<210> SEQ ID NO 9
<211> LENGTH: 37
<212> TYPE: DNA
<213> ORGANISM: Artificial Sequence
<220> FEATURE:
<223> OTHER INFORMATION: Reverse MET primer

<400> SEQUENCE: 9
ctggtcgtgt gcccacctca tcatcagcgt tatcttc                            37
```

IDENTIFICATION OF NOVEL ANTI-FIBROTIC PEPTIDE IN C-TERMINAL REGION OF THE MET RECEPTOR TYROSINE KINASE

CROSS-REFERENCE TO RELATED APPLICATIONS

This application is the U.S. national phase application filed under 35 U.S.C. § 371 claiming benefit to International Patent Application No. PCT/US2016/043376, filed on Jul. 21, 2016, which is entitled to priority under 35 U.S.C. § 119(e) to U.S. provisional Application No. 62/197,923, filed Jul. 28, 2015, the disclosures of which are incorporated herein by reference in their entirety.

STATEMENT REGARDING FEDERALLY SPONSORED RESEARCH OR DEVELOPMENT

This invention was made with government support under P60 AR062755-01 awarded by the National Institutes of Health (NIH). The government has certain rights in the invention.

BACKGROUND OF THE INVENTION

Hepatocyte growth factor (HGF) has anti-fibrogenic properties. However, several studies have shown that HGF only affects fibroblasts expressing the HGF receptor known as cellular mesenchymal-epithelial transition factor (c-MET, MET). During fibrotic diseases, such as scleroderma, pulmonary fibrosis and hepatic fibrosis, c-MET is found to be overexpressed and HGF to be at elevated concentrations compared to normal, indicating their function in a biological feedback process to deal with increasing collagen levels. However, the elevated levels are insufficient to regulate the fibrotic process.

Pulmonary fibrosis is the most severe complication and the leading cause of mortality in scleroderma. Although SSc-ILD is detected in more than 90% of patients (D'Angelo W A, et al., Am J Med., 1969, 46(3):428-40 and Steen V D, et al., Ann Rheum Dis., 2007, 66(7):940-4), disease progression is very heterogeneous, suggesting that SSc-ILD patients have some biological or genetic factors that differentially affect the pathogenic mechanisms of the disease. African American SSc patients exhibit higher prevalence of ILD and worse outcomes than those of other races (Nietert P J, et al., J Rheumatol, 2006, 33:263-268 and Silver R M, et al., Curr Opin Rheumatol., 2012, 24(6):642-8). It was previously reported that a cell-protective and anti-fibrotic agent, HGF, is downregulated in bronchoalveolar lavage fluid (BALF) and plasma from African American SSc-ILD patients compared with white SSc-ILD patients. Moreover, in SSc lung fibroblasts from white patients, HGF downregulates extracellular matrix proteins such as collagen and connective tissue growth factor (CTGF, CCN2), whereas in SSc fibroblasts from African Americans, HGF is not functional due to a deficiency in phosphorylation of the MET receptor (Bogatkevich G S, et al., Arthritis Rheum, 2007, 56:2432-42 and Bogatkevich G S, et al., Arthritis Rheum, 2007, 56:3468-77).

MET is a receptor tyrosine kinase implicated in embryonic development and tissue regeneration after acute injury (Ohmichi H, et al., Development, 1998, 125(7):1315-24 and Neuss S, et al., Stem Cells, 2004, 22:405-14). Following binding of HGF, MET undergoes auto phosphorylation at tyrosine residues in its cytoplasmic domain and initiates a cascade of signal transduction events leading to specific cellular responses (Stuart K A, et al., Int J Exp Pathol, 2000, 81:17-30 and Hammond D E, et al., Curr Top Microbiol Immunol, 2004, 286:21-44). Several studies have characterized the anti-fibrotic effects of MET on collagen, MMP-1, and CTGF in SSc skin fibroblasts (Jinnin M, et al., J Invest Dermatol, 2005, 124:324-30 and Sherriff-Tadano R, et al., Mod Rheumatol, 2006, 16:364-71).

The benefit of the overexpression of c-MET has been recognized in studies examining cardiac scarring, skin scleroderma, and hepatic fibrosis and has been proposed as a therapeutic approach. However, c-MET exhibits oncogenic properties which can be a problem.

Despite the advances made in the art for treatment of diseases and disorders involving the use of c-MET based therapy, there is a need in the art for improved compositions useful for the treatment of fibrotic diseases and disorders. The present invention fulfills these needs.

SUMMARY OF THE INVENTION

In one embodiment, the invention relates to an isolated C-terminal peptide of the MET receptor having anti-fibrotic activity, wherein the peptide comprises an amino acid sequence selected from the group consisting of SEQ ID NO: 1, SEQ ID NO: 4 and a variant thereof.

In one embodiment, the isolated peptide comprises a caspase-3 cleavage site. In one embodiment, the isolated peptide comprises an amino acid sequence selected from the group consisting of SEQ ID NO: 2, SEQ ID NO: 3, SEQ ID NO: 5, SEQ ID NO: 6, SEQ ID NO: 7 and a variant thereof.

In one embodiment, the the N-terminus of the peptide is acetylated.

In one embodiment, the invention relates to an isolated polynucleotide encoding a C-terminal peptide of the MET receptor having anti-fibrotic activity, wherein the peptide comprises an amino acid sequence selected from the group consisting of SEQ ID NO: 1, SEQ ID NO: 4 and a variant thereof. In one embodiment, the polynucleotide is operably linked to a promoter.

In one embodiment, the invention relates to an expression vector comprising an isolated polynucleotide encoding a C-terminal peptide of the MET receptor having anti-fibrotic activity, wherein the peptide comprises an amino acid sequence selected from the group consisting of SEQ ID NO: 1, SEQ ID NO: 4 and a variant thereof. In one embodiment, the invention relates to an isolated host cell transformed with an expression vector for expression of a C-terminal peptide of the MET receptor having anti-fibrotic activity.

In one embodiment, the invention relates to a pharmaceutical composition comprising an isolated peptide comprising a C-terminal peptide of the MET receptor having anti-fibrotic activity, wherein the peptide comprises an amino acid sequence selected from the group consisting of SEQ ID NO: 1, SEQ ID NO: 4, or an isolated polynucleotide encoding the peptide, and a pharmaceutically acceptable carrier.

In one embodiment, the invention relates to a method of treating a subject with fibrosis, the method comprising administering to the subject a therapeutically effective amount of the composition comprising an isolated peptide comprising a C-terminal peptide of the MET receptor having anti-fibrotic activity, wherein the peptide comprises an amino acid sequence selected from the group consisting of SEQ ID NO: 1, SEQ ID NO: 4, or an isolated polynucleotide encoding the peptide, thereby treating the subject with fibrosis. In one embodiment, the subject has a fibrosis of the skin. In one embodiment, the subject has scleroderma. In one embodiment, the subject has idiopathic pulmonary fibrosis. In one embodiment, the subject has scleroderma associated interstitial lung disease. In one embodiment, the fibrosis is selected from the group consisting of kidney fibrosis, liver fibrosis, cardiac fibrosis, pulmonary fibrosis, restenosis-related vascular fibrosis, spleen fibrosis, age-related fibrosis, skin fibrosis, and post-transplantation fibrosis.

In one embodiment, the method of treating a subject with fibrosis further comprises administering to the subject a therapeutically effective amount of a therapeutic agent. In one embodiment, the therapeutic agent is selected from the group consisting of an anti-inflammatory agent, an immunosuppressive agent, an anti-diabetic agent, digoxin, a vasodilator, an angiotensin II converting enzyme (ACE) inhibitors, an angiotensin II receptor blockers (ARB), a calcium channel blocker, an isosorbide dinitrate, a hydralazine, a nitrate, a hydralazine, a beta-blocker, a natriuretic peptides, a heparinoid, and a connective tissue growth factor inhibitor.

In one embodiment, the invention relates to a method of negatively regulating TGF-β signaling pathway in a cell, the method comprising contacting the cell with an effective amount of a peptide comprising a C-terminal peptide of the MET receptor having anti-fibrotic activity, wherein the peptide comprises an amino acid sequence selected from the group consisting of SEQ ID NO: 1, SEQ ID NO: 4, or a polynucleotide encoding the peptide, thereby negatively regulating TGF-β signaling pathway in a cell.

In one embodiment, the invention relates to a method of diagnosing a fibrotic disease or disorder in a subject, the method comprising detecting the presence of the D1398G MET receptor mutant in the subject. In one embodiment, the method further comprises treating the diagnosed patient with an anti-fibrotic therapy. In one embodiment, the anti-fibrotic therapy comprises administering a pharmaceutical composition comprising an isolated peptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 and a variant thereof or an isolated polynucleotide encoding the peptide to the patient. In one embodiment, the method further comprises administering to the subject a therapeutically effective amount of a therapeutic agent.

In one embodiment, the invention relates to a method of inhibiting apoptosis in a cell, the method comprising contacting a cell with an effective amount of a peptide comprising a caspase-3 cleavage site, or a polynucleotide encoding the peptide, thereby inhibiting apoptosis in the cell. In one embodiment, the peptide comprises an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 and a variant thereof.

In one embodiment, the invention relates to a kit for diagnosing a fibrotic disease or disorder in a subject, comprising a probe for the D1398G MET receptor mutant.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIG. 1A depicts a time course of MET WT and MET D1398G tyrosine phosphorylation as determined in LF and AEC incubated with HGF (50 ng/ml) for various time points. Cell extracts were immunoblotted with anti-phospho-MET or anti-MET polyclonal antibodies (see details in Materials and Methods). FIG. 1B depicts quantitative results of densitometric analysis of immunoblots. Values are the mean and SD from three independent experiments.

FIG. 2, comprising FIG. 2A depicts transfected SSc LF were serum-starved for 24 hours followed by incubation for 48 hours with recombinant HGF (50 ng/ml). The cells were collected with lysis buffer and analyzed by Western blot with indicated antibodies including MET as a transfection efficiency control. Anti-β-actin antibody was used as a loading control. FIG. 2B depicts quantitative results of densitometric analysis of immunoblots. Values are the mean and SD from four independent experiments.

FIG. 3, comprising FIG. 3A depicts that the cells were collected with lysis buffer and analyzed by Western blot with indicated antibodies including MET as a transfection efficiency control and anti-β-actin antibody as a loading control. FIG. 3B through FIG. 3D depict densitometric analysis of immunoblots for collagen, SMA and CCN2 respectively. Values are the mean and SD from three independent experiments.

FIG. 4, comprising FIG. 4A depicts HGF-induced Erk1/2 phosphorylation in LF and AEC transfected with MET WT and MET D1398G was determined in cells treated with HGF (50 ng/ml) for 10 min. Cell extracts were immunoblotted with anti-phospho-Erk1/2 or anti-Erk1/2, anti-MET, and anti-β-actin antibodies. FIG. 4B depicts densitometric analysis of phospho-Erk1/2 immunoblots from three independent experiments. FIG. 4C and FIG. 4D depict Ras activity in LF and AEC respectively, transfected with MET WT and MET D1398G treated with and without HGF (50 ng/ml) for 10 min. Values are the mean and SD from three independent experiments; *Statistically significant differences between cells stimulated with HGF versus control ($p<0.05$).

FIG. 5, comprising FIG. 5A depicts transfected cells were incubated with or without cisplatin for 24 hours. The cells were collected with lysis buffer and analyzed by Western blot with indicated antibodies. FIG. 5B depicts densitometric analysis of uncleaved MET detected by C12 antibody. Values are the mean and SD from three independent experiments.

FIG. 6, comprising FIG. 6A depicts lung sections stained with hematoxylin and eosin (H&E). FIG. 6B and FIG. 6C depict immunofluorescent images stained with anti-MET 4F8.2 antibody detecting total (cleaved and uncleaved MET) (FIG. 6B); anti-MET antibody C12 that does not recognize MET after C-terminal cleavage (FIG. 6C); nuclei are stained with 4',6-diamidino-2-phenylindole (DAPI). Representative images from three patients with SSc-ILD are presented. FIG. 6D depicts quantitative results of image analysis for MET 4F8.2- and MET C12-positive cells. Cells (total, 4F8.2 positive and MET C12 positive) were counted on six randomly selected, nonoverlapping, high-power fields per sample at ×400 magnification, and presented as mean±SD.

FIG. 8, comprising FIG. 8A through FIG. 8D depicts basic properties of the M10 peptide.

FIG. 9, comprising FIG. 9A through FIG. 9I depicts intracellular localization of M10.

FIG. 10, comprising FIG. 10A and FIG. 10C depict SSc lung and skin fibroblasts respectively were serum starved for 24 hours followed by incubation for 48 hours with indicated concentrations of M10 or scrambled peptide (Scr). Cells were collected with lysis buffer and analyzed by Western blot with anticollagen type I and anti-β-actin antibody as a loading control. FIG. 10B and FIG. 10D, depict densitometric analysis of the immunoblots from FIG. 10A and FIG. 10C respectively. Values are the mean and standard deviation from 3 independent experiments. *P<0.05 and **P<0.01 vs unstimulated cells. SSc, systemic sclerosis.

FIG. 11, comprising FIG. 11A depicts MRC5 cells, normal lung fibroblasts, and normal skin fibroblasts were incubated with or without M10, scrambled peptide (Scr), and TGFβ for 48 hours in serum-free medium. Cell extracts were immunoblotted with anti-collagen type I and anti-β-actin antibodies. FIG. 11B depicts densitometric analysis of collagen type I immunoblots from 2 independent experiments. Values are the mean and standard deviation from 3 independent experiments; *statistically significant differences between cells stimulated with M10 and TGFβ vs TGFβ (P<0.01).

FIG. 12, comprising FIG. 12A depicts M10 in complex with Smad2. The interactive visualization of statistically significant (P<0.02) binding of M10 (amino acids pro-3, ala-4, trp-7, glu-8, thr-9, and ser-10) with Mad Homology 2 domain of Smad2. FIG. 12B depicts M10 interacts with Smad2 but not Smad4. DDK-tagged recombinant Smad2 and Smad4 were incubated with M10 as detailed in the Materials and Methods. Interacting complexes were captured with protein G sepharose and subjected to immunoblotting with anti-DDK antibody. Peptide-protein interacting mixture (M) was used as a positive control. E stands for eluted interacting complexes. FIG. 12C depicts coimmunoprecipitation of M10 and Smad2 in scleroderma lung (lanes 1 and 2) and skin (lanes 3 and 4) fibroblasts. Cells were cultured in 100-mm plates to confluence, serum-starved overnight, incubated with M10, or scrambled peptide (Scr) for 24 hours; collected; and subjected to immunoprecipitation as outlined in the experimental procedures. SSc, systemic sclerosis.

FIG. 13, comprising FIG. 13A depicts colocalization of Smad2 and M10 in lung fibroblasts cultured in serum-free medium without TGFβ (panels 1, 2, and 3) and with TGFβ (panels 4, 5, and 6). FIG. 13B depicts M10 reduces TGFβ-induced Smad2 phosphorylation in normal lung and skin fibroblasts. Cells were cultured on 6-well plates to 90% confluence, serum-starved overnight, incubated with or without M10, or scrambled peptide (Scr) and TGFβ and subjected to immunoblotting.

FIG. 14, comprising FIG. 14A depicts representative histologic findings of lung inflammation and fibrosis. 1—control 1 (saline+scrambled peptide), 2—control 2 (saline+M10), 3—bleomycin+scrambled peptide, 4—bleomycin+M10. FIG. 14B depicts a quantitative evaluation of fibrotic changes (Ashcroft scores), n=32 (8 mice per group). FIG. 14C depicts lung collagen content determined by Sircol assay, n=24 (6 mice per group). Values in B and C are the mean±standard deviation. *Statistically significant differences (P<0.05) between bleomycin-challenged mice treated with M10 and scrambled peptide.

FIG. 16, comprising

FIG. 17, comprising FIG. 17A depicts 1403 and 1404 peptides inhibit collagen in TGFβ-stimulated LF. Cells were incubated with and without TGFβ (5 ng/ml), 1403, and 1404 peptides (1 µg/ml) or scrambled peptide (Control, Co) for 24 h and analyzed by immunoblotting using anti-collagen type I antibody. FIG. 17B depicts 1403 and 1404 but not M10 protect AEC from FasL- and cisplatin-induced apoptosis. AEC were incubated with or without 1403, 1404, or scrambled (Control) peptides, FasL, and cisplatin for 24 hours and analyzed by Caspase 3 Assay from Abcam.

DETAILED DESCRIPTION OF THE INVENTION

Figures 1A, 1B:
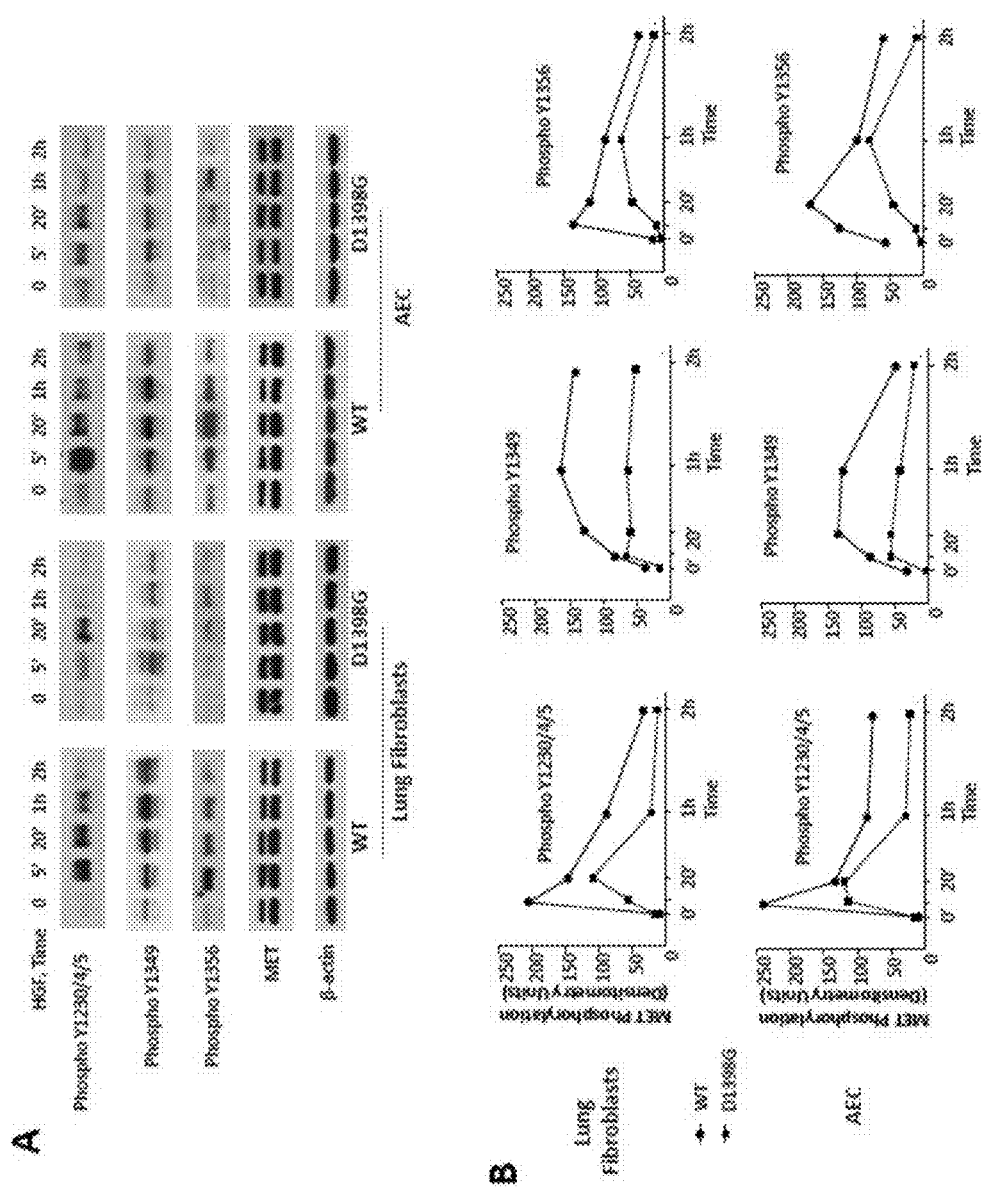
FIG. 1A and FIG. 1B, depicts MET tyrosine phosphorylation in lung fibroblasts (LF) and alveolar epithelial cells (AEC).

The present invention relates to compositions and methods for negatively modulating TGF-β signaling pathways. In one embodiment, the composition is an anti-fibrotic peptide comprising a C-terminal amino acid sequence of the MET receptor or otherwise referred to as MET receptor tyrosine kinase. In one embodiment, the anti-fibrotic peptide comprises a C-terminal amino acid sequence of the MET receptor, but does not include full length MET receptor. In one embodiment, the anti-fibrotic peptide comprises the amino acid sequence of SEQ ID NO: 1. In one embodiment, the anti-fibrotic peptide comprises the amino acid sequence of SEQ ID NO: 4.

In one embodiment, the anti-fibrotic peptide comprises a C-terminal amino acid sequence of the MET receptor and further comprising a caspase-3 cleavage site. In various embodiments, the peptide comprises SEQ ID NO: 2, SEQ ID NO: 3, SEQ ID NO: 5, SEQ ID NO: 6, SEQ ID NO: 7, or variants thereof.

In one embodiment, the anti-fibrotic peptide comprises a C-terminal amino acid sequence of the MET receptor and further comprising a caspase-3 cleavage site and an N-terminal aspartic acid. In various embodiments, the peptide comprises SEQ ID NO: 3, SEQ ID NO: 7 or variants thereof.

In one embodiment, the invention relates to polynucleotide sequences encoding a peptide of the invention. In one embodiment, the polynucleotide encodes a peptide selected from SEQ ID NO: 1, SEQ ID NO: 2, SEQ ID NO: 3, SEQ ID NO: 4, SEQ ID NO: 5, SEQ ID NO: 6, SEQ ID NO: 7 or variants thereof.

In one embodiment, the invention provides compositions and methods for inhibiting fibrosis. In one embodiment, the invention provides compositions and methods for treating a patient suffering from fibrosis. In one embodiment, the method comprises administering to a patient in need thereof, a compound consisting of one or more of an anti-fibrotic peptide of the invention, a polynucleotide encoding a peptide of the invention, analogs, derivatives, variants and pharmaceutically-acceptable salts thereof, at a therapeutically effective amount to treat the fibrotic disease or disorder.

In one embodiment, the invention provides compositions and methods for inhibiting apoptosis. In one embodiment, the method comprises contacting a cell with a peptide of the invention or a polynucleotide encoding a peptide of the invention. In one embodiment, the method comprises administering a peptide of the invention or a polynucleotide encoding a peptide of the invention to a patient in need thereof.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology can be used.

It is also to be understood that the terminology used herein is for the purpose of describing particular embodiments only, and is not intended to be limiting.

The articles "a" and "an" are used herein to refer to one or to more than one (i.e. to at least one) of the grammatical object of the article. By way of example, "an element" means one element or more than one element.

As used herein, the term "about" can be understood by persons of ordinary skill in the art and will vary to some extent on the context in which it is used. As used herein when referring to a measurable value such as an amount, a temporal duration, and the like, the term "about" is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "biomarker" is a characteristic that is objectively measured and evaluated as an indicator of normal biological processes, pathological processes, or pharmacological responses to a therapeutic intervention. The biomarker can for example describe a substance whose detection indicates a particular disease state. The biomarker may be a peptide that causes disease or is associated with susceptibility to disease. In some instances, the biomarker may be a gene that causes disease or is associated with susceptibility to disease. In other instances, the biomarker is a metabolite. In any event, the biomarker can be differentially present (i.e., increased or decreased) in a biological sample from a subject or a group of subjects having a first phenotype (e.g., having a disease) as compared to a biological sample from a subject or group of subjects having a second phenotype (e.g., not having the disease). A biomarker is preferably differentially present at a level that is statistically significant (i.e., a p-value less than 0.05 and/or a q-value of less than 0.10 as determined using either Welch's T-test or Wilcoxon's rank-sum Test).

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health. Preferably, the animal is a mammal. More preferably, the mammal is a human.

A disease or disorder is "alleviated" if the severity of a sign or symptom of the disease or disorder, the frequency with which such a sign or symptom is experienced by a patient, or both, is reduced.

The term "comparator control,", as used herein, relates to presence of a mutant or level of expression or activity which may be determined at the same time as the test sample by using a sample previously collected and stored from a subject whose disease state is/are known.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Effective amount" refers to an amount of a compound, formulation, material, or composition, as described herein effective to achieve a particular biological result.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Instructional material," as that term is used herein, includes a publication, a recording, a diagram, or any other medium of expression which can be used to communicate the usefulness of the nucleic acid, peptide, and/or compound of the invention in the kit for identifying, diagnosing or alleviating or treating the various diseases or disorders recited herein. Optionally, or alternately, the instructional material may describe one or more methods of identifying, diagnosing or alleviating the diseases or disorders in a cell or a tissue of a subject. The instructional material of the kit may, for example, be affixed to a container that contains the nucleic acid, peptide, and/or compound of the invention or be shipped together with a container that contains the nucleic acid, peptide, and/or compound. Alternatively, the instructional material may be shipped separately from the container with the intention that the recipient uses the instructional material and the compound cooperatively.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

"Measuring" or "measurement," or alternatively "detecting" or "detection," or alternatively "determine" or "determining" means assessing the presence, absence, quantity or amount of either a given substance within a clinical or subject-derived sample, including the derivation of qualitative or quantitative concentration levels of such substances.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

"Scleroderma" as used herein refers to a chronic autoimmune disease characterized by fibrosis (or hardening), vascular alterations, and autoantibodies. There are two major forms, one is a systemic form that includes limited cutaneous scleroderma mainly affects the hands, arms and face, although pulmonary hypertension is frequent. Diffuse cutaneous scleroderma (or systemic sclerosis) is rapidly progressing and affects a large area of the skin and one or more internal organs, frequently the kidneys, esophagus, heart and lungs. Systemic scleroderma in both of its forms can be fatal. The other form of scleroderma is a localized form that has two subtypes: morphea and linear scleroderma. The peptides of the invention can be used to treat any form of scleroderma.

As used herein, the term "substantially reverse fibrosis" refers to where the fibrotic material or components under treatment in a target tissue or organ has been decreased or altogether eradicated. Substantial reversal of fibrosis preferably refers to where least about 10%, or about 25%, or about 50%, or more preferably by at least about 75%, or more preferably by about 85%, or still more preferably by about 90%, or more preferably still about by 95%, or more preferably still by 99% or more of the fibrotic components or material has been removed as compared to pre-treatment.

A "therapeutic" treatment is a treatment administered to a subject who exhibits a sign or symptom of pathology, for the purpose of diminishing or eliminating that sign or symptom.

As used herein, the terms "therapy" or "therapeutic regimen" refer to those activities taken to alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more drugs or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "variant," as used herein, refers to a compound that differs from the compound of the present invention, but retains essential properties thereof. A non-limiting example of this is a polynucleotide or polypeptide compound having conservative substitutions with respect to the reference compound, commonly known as degenerate variants. Another non-limiting example of a variant is a compound that is structurally different, but retains the same active domain of the compounds of the present invention. Variants include N-terminal or C-terminal extensions, capped amino acids, modifications of reactive amino acid side chain functional groups, e.g., branching from lysine residues, pegylation, and/or truncations of a polypeptide compound. Generally, variants are overall closely similar, and in many regions, identical to the compounds of the present invention. Accordingly, the variants may contain alterations in the coding regions, non-coding regions, or both.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides compositions and methods for treating fibrotic diseases using a 2 kD C-terminal fragment (M10) of the MET receptor and derivatives and variants thereof. In one embodiment, the 2 kD C-terminal fragment (M10) of the MET receptor comprises the amino acid sequence of TRPASFWETS (SEQ ID NO: 1). In one embodiment, the peptide of the invention exhibits anti-fibrotic properties.

The present invention provides compositions and methods for treating fibrotic diseases using the M5 peptide, a C-terminal fragment of the MET receptor. In another embodiment, the M5 peptide of the invention comprises the amino acid sequence of TRPAS (SEQ ID NO: 4).

The present invention provides compositions and methods for treating fibrotic diseases using a C-terminal fragment of the MET receptor with added caspase-3 cleavage sites. In one embodiment, the peptide comprises the M5 peptide with added caspase-3 cleavage sites. In one embodiment, the peptide comprises the 1404 peptide, comprising the amino acid sequence of DEVDTRPAS (SEQ ID NO: 2). In one embodiment, the peptide comprises the M10 peptide with added caspase-3 cleavage sites. In one embodiment, the peptide comprises the amino acid sequence of DEVDTRPASFWETS (SEQ ID NO: 6).

The present invention also provides compositions and methods for treating fibrotic diseases using a C-terminal fragment of the MET receptor with added caspase-3 cleavage sites with an additional aspartic acid. In one embodiment, the peptide comprises the M5 peptide with added caspase-3 cleavage sites and an additional N-terminal aspartic acid. In one embodiment, the peptide consists of the 1403 peptide, comprising the amino acid sequence of DDEVDTRPAS (SEQ ID NO: 3). In one embodiment, the peptide comprises the M10 peptide with added caspase-3 cleavage sites and an additional N-terminal aspartic acid. In one embodiment, the peptide consists of a peptide comprising the amino acid sequence of DDEVDTRPASFWETS (SEQ ID NO: 7).

The present invention also provides compositions and methods for inhibition of apoptosis using a peptide or a polynucleotide encoding a peptide of the invention. In one embodiment, the peptide comprises an amino acid sequence as set forth in SEQ ID NO: 1, SEQ ID NO: 2, SEQ ID NO: 3, SEQ ID NO: 4, SEQ ID NO: 5, SEQ ID NO: 6 and SEQ ID NO: 7.

The invention is based on the identification that the 2 kD C-terminal fragment (M10) of the MET receptor is a peptide having robust anti-fibrotic properties. For example, purified M10 markedly reduced collagen and other extracellular matrix proteins in scleroderma lung fibroblasts and in TGF-β-stimulated normal lung fibroblasts. Accordingly, the invention provides a novel anti-fibrotic peptide that negatively modulates TGF-β signaling pathways.

In some embodiments, methods are disclosed for inhibiting fibrosis in vivo or in vitro. In additional embodiments, methods are disclosed for the treatment of fibrosis in a subject. Fibrosis includes but is not limited to kidney fibrosis, liver fibrosis, cardiac fibrosis, pulmonary fibrosis, restenosis-related vascular fibrosis, spleen fibrosis, age-related fibrosis, skin fibrosis, and post-transplantation fibrosis.

In some specific non-limiting examples, the compositions of the invention can be used to treat a subject having scleroderma or pulmonary fibrosis.

Compositions

C-terminal MET receptor peptides are disclosed herein that have anti-fibrotic activity. In some embodiments, these peptides comprise an amino acid sequence as set forth in SEQ ID NO: 1, SEQ ID NO: 2, SEQ ID NO: 3, SEQ ID NO: 4, SEQ ID NO: 5, SEQ ID NO: 6, SEQ ID NO: 7 and variants thereof. The invention also includes polynucleotides encoding these peptides and host cells transformed with the polynucleotides. Methods of using these peptides and polynucleotides are disclosed. In one example, the peptide includes a modification with acetylated N-terminus.

The invention provides peptides and isolated nucleic acids encoding them. Also provided are vectors and cells comprising an isolated nucleic acid of the invention. The peptides, including peptides and analogs, fragments, and derivatives thereof are based on a C-terminal fragment of the MET receptor.

In one embodiment, the peptides of the invention are human. Exemplary peptides of the present invention are set forth in SEQ ID NO: 1, SEQ ID NO: 2, SEQ ID NO: 3, SEQ ID NO: 4, SEQ ID NO: 5, SEQ ID NO: 6 and SEQ ID NO: 7. In one embodiment, the composition comprises an isolated nucleic acid encoding a peptide of the invention. For example, in one embodiment, the composition comprises an isolated nucleic acid encoding a peptide having an amino acid sequence as set forth in SEQ ID NO: 1, SEQ ID NO: 2, SEQ ID NO: 3, SEQ ID NO: 4, SEQ ID NO: 5, SEQ ID NO: 6 and SEQ ID NO: 7.

In one embodiment, the invention includes variants of the peptides of the invention. In one embodiment, variants differ from naturally-occurring peptides by conservative amino acid sequence differences or by modifications which do not affect sequence, or by both. For example, conservative amino acid changes may be made, which although they alter the primary sequence of the peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

In one embodiment, the peptide of the invention comprises a peptide having at least 75% homology with SEQ ID NO: 1. In one embodiment, the peptide of the invention comprises a peptide having at least 80% homology with SEQ ID NO: 1. In one embodiment, the peptide of the invention comprises a peptide having at least 85% homology with SEQ ID NO: 1. In one embodiment, the peptide of the invention comprises a peptide having at least 90% homology with SEQ ID NO: 1. In one embodiment, the peptide of the invention comprises a peptide having at least 95% homology with SEQ ID NO: 1. In one embodiment, the peptide of the invention comprises a peptide having at least 99% homology with SEQ ID NO: 1. In a further embodiment, the peptide of the invention comprise D-, L-, and unnatural isomers of amino acids.

In one embodiment, the peptide of the invention comprises a peptide having at least 75% homology with SEQ ID NO: 2. In one embodiment, the peptide of the invention comprises a peptide having at least 80% homology with SEQ ID NO: 2. In one embodiment, the peptide of the invention comprises a peptide having at least 85% homology with SEQ ID NO: 2. In one embodiment, the peptide of the invention comprises a peptide having at least 90% homology with SEQ ID NO: 2. In one embodiment, the peptide of the invention comprises a peptide having at least 95% homology with SEQ ID NO: 2. In one embodiment, the peptide of the invention comprises a peptide having at least 99% homology with SEQ ID NO: 2. In a further embodiment, the peptide of the invention comprise D-, L-, and unnatural isomers of amino acids.

In one embodiment, the peptide of the invention comprises a peptide having at least 75% homology with SEQ ID NO: 3. In one embodiment, the peptide of the invention comprises a peptide having at least 80% homology with SEQ ID NO: 3. In one embodiment, the peptide of the invention comprises a peptide having at least 85% homology with SEQ ID NO: 3. In one embodiment, the peptide of the invention comprises a peptide having at least 90% homology with SEQ ID NO: 3. In one embodiment, the peptide of the invention comprises a peptide having at least 95% homology with SEQ ID NO: 3. In one embodiment, the peptide of the invention comprises a peptide having at least 99% homology with SEQ ID NO: 3. In a further embodiment, the peptide of the invention comprise D-, L-, and unnatural isomers of amino acids.

In one embodiment, the peptide of the invention comprises a peptide having at least 75% homology with SEQ ID NO: 4. In one embodiment, the peptide of the invention comprises a peptide having at least 80% homology with SEQ ID NO: 4. In one embodiment, the peptide of the invention comprises a peptide having at least 85% homology with SEQ ID NO: 4. In one embodiment, the peptide of the invention comprises a peptide having at least 90% homology with SEQ ID NO: 4. In one embodiment, the peptide of the invention comprises a peptide having at least 95% homology with SEQ ID NO: 4. In one embodiment, the peptide of the invention comprises a peptide having at least 99% homology with SEQ ID NO: 4. In a further embodiment, the peptide of the invention comprise D-, L-, and unnatural isomers of amino acids.

In one embodiment, the peptide of the invention comprises a peptide having at least 75% homology with SEQ ID NO: 5. In one embodiment, the peptide of the invention comprises a peptide having at least 80% homology with SEQ ID NO: 5. In one embodiment, the peptide of the invention comprises a peptide having at least 85% homology with SEQ ID NO: 5. In one embodiment, the peptide of the invention comprises a peptide having at least 90% homology with SEQ ID NO: 5. In one embodiment, the peptide of the invention comprises a peptide having at least 95% homology with SEQ ID NO: 5. In one embodiment, the peptide of the invention comprises a peptide having at least 99% homology with SEQ ID NO: 5. In a further embodiment, the peptide of the invention comprise D-, L-, and unnatural isomers of amino acids.

In one embodiment, the peptide of the invention comprises a peptide having at least 75% homology with SEQ ID NO: 6. In one embodiment, the peptide of the invention comprises a peptide having at least 80% homology with SEQ ID NO: 6. In one embodiment, the peptide of the invention comprises a peptide having at least 85% homology with SEQ ID NO: 6. In one embodiment, the peptide of the invention comprises a peptide having at least 90% homology with SEQ ID NO: 6. In one embodiment, the peptide of the invention comprises a peptide having at least 95% homology with SEQ ID NO: 6. In one embodiment, the peptide of the invention comprises a peptide having at least 99% homology with SEQ ID NO: 6. In a further embodiment, the peptide of the invention comprise D-, L-, and unnatural isomers of amino acids.

In one embodiment, the peptide of the invention comprises a peptide having at least 75% homology with SEQ ID NO: 7. In one embodiment, the peptide of the invention comprises a peptide having at least 80% homology with SEQ ID NO: 4. In one embodiment, the peptide of the invention comprises a peptide having at least 85% homology with SEQ ID NO: 7. In one embodiment, the peptide of the invention comprises a peptide having at least 90% homology with SEQ ID NO: 7. In one embodiment, the peptide of the invention comprises a peptide having at least 95% homology with SEQ ID NO: 7. In one embodiment, the peptide of the invention comprises a peptide having at least 99% homology with SEQ ID NO: 7. In a further embodiment, the peptide of the invention comprise D-, L-, and unnatural isomers of amino acids. As known in the art the "similarity" between two peptides is determined by comparing the amino acid sequence and its conserved amino acid substitutes of one polypeptide to a sequence of a second peptide. Variants are defined to include polypeptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to bind to ubiquitin or to a ubiquitylated protein.

The present invention includes amino acid sequences that are at least 60%, 65%, 70%, 72%, 74%, 76%, 78%, 80%, 90%, or 95% similar or identical to the original amino acid sequence. The degree of identity between two polypeptides is determined using computer algorithms and methods that are widely known for the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

Variants of suitable peptides of the invention can also be expressed. Variants may be made by, for example, the deletion, addition, or alteration of amino acids that have either (i) minimal influence on certain properties, secondary structure, and hydropathic nature of the polypeptide or (ii) substantial effect on one or more properties of the peptide mimetics of the invention.

Variants may also include, for example, a peptide conjugated to a linker or other sequence for ease of synthesis, purification, identification, or therapeutic use (i.e., delivery) of the peptide.

The variants of the peptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the peptide is an alternative splice variant of the peptide of the present invention, (iv) fragments of the peptides and/or (v) one in which the peptide is fused with another peptide, such as a leader or secretory sequence or a sequence which is employed for purification (for example, His-tag) or for detection (for example, Sv5 epitope tag). The fragments include peptides generated via proteolytic cleavage (including multi-site proteolysis) of an original sequence. Variants may be post-translationally, or chemically modified. Such variants are deemed to be within the scope of those skilled in the art from the teaching herein.

The peptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or *Xenopus* egg extracts (U.S. Pat. No. 6,103,489) to a standard translation reaction.

The peptides of the invention may be conjugated with other molecules, such as proteins, to prepare fusion proteins. This may be accomplished, for example, by the synthesis of N-terminal or C-terminal fusion proteins provided that the resulting fusion protein retains the functionality of the peptide of the invention.

The peptides of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benzenesulfonic acid, and toluenesulfonic acids.

Peptides of the invention may also have modifications. Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are peptides which have been modified using ordinary molecular biological techniques so as to improve their resistance to proteolytic degradation or to optimize solubility properties or to render them more suitable as a therapeutic agent. Such variants include those containing residues other than naturally-occurring L-amino acids, e.g., D-amino acids or non-naturally-occurring synthetic amino acids. The peptides of the invention may further be conjugated to non-amino acid moieties that are useful in their therapeutic application. In particular, moieties that improve the stability, biological half-life, water solubility, and/or immunologic characteristics of the peptide are useful. A non-limiting example of such a moiety is polyethylene glycol (PEG).

A peptide of the invention may be synthesized by conventional techniques. For example, the peptides of the invention may be synthesized by chemical synthesis using solid phase peptide synthesis. These methods employ either solid or solution phase synthesis methods (see for example, J. M. Stewart, and J. D. Young, Solid Phase Peptide Synthesis, $2^{nd}$ Ed., Pierce Chemical Co., Rockford Ill. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, suprs, Vol 1, for classical solution synthesis.)

The peptides may be chemically synthesized by Merrifield-type solid phase peptide synthesis. This method may be routinely performed to yield peptides up to about 60-70 residues in length, and may, in some cases, be utilized to make peptides up to about 100 amino acids long. Larger peptides may also be generated synthetically via fragment condensation or native chemical ligation (Dawson et al., 2000, Ann. Rev. Biochem. 69:923-960). An advantage to the utilization of a synthetic peptide route is the ability to produce large amounts of peptides, even those that rarely occur naturally, with relatively high purities, i.e., purities sufficient for research, diagnostic or therapeutic purposes.

The peptides of the invention may be prepared by standard chemical or biological means of peptide synthesis. Biological methods include, without limitation, expression of a nucleic acid encoding a peptide in a host cell or in an in vitro translation system.

Included in the invention are nucleic acid sequences that encode the peptide of the invention. In one embodiment, the invention includes nucleic acid sequences encoding an amino acid sequence as set forth in SEQ ID NO: 1, SEQ ID NO: 2, SEQ ID NO: 3, SEQ ID NO: 4, SEQ ID NO: 5, SEQ ID NO: 6 and SEQ ID NO: 7. Accordingly, subclones of a nucleic acid sequence encoding a peptide of the invention can be produced using conventional molecular genetic manipulation for subcloning gene fragments, such as described by Sambrook et al., *Molecular Cloning: A Laboratory Manual*, Cold Springs Laboratory, Cold Springs Harbor, N.Y. (2012), and Ausubel et al. (ed.), *Current Protocols in Molecular Biology*, John Wiley & Sons (New York, N.Y.) (1999 and preceding editions), each of which is hereby incorporated by reference in its entirety. The subclones then are expressed in vitro or in vivo in bacterial cells to yield a smaller protein or polypeptide that can be tested for a particular activity.

Biological preparation of a peptide of the invention involves expression of a nucleic acid encoding a desired peptide. An expression cassette comprising such a coding sequence may be used to produce a desired peptide for use in the method of the invention.

In the context of an expression vector, the vector can be readily introduced into a host cell, e.g., mammalian, bacterial, yeast or insect cell by any method in the art. Coding sequences for a desired peptide of the invention may be codon optimized based on the codon usage of the intended host cell in order to improve expression efficiency as demonstrated herein. Codon usage patterns can be found in the literature (Nakamura et al., 2000, Nuc Acids Res. 28:292). Representative examples of appropriate hosts include bacterial cells, such as streptococci, staphylococci, *E. coli*, *Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

The expression vector can be transferred into a host cell by physical, biological or chemical means. Physical methods for introducing a polynucleotide into a host cell include calcium phosphate precipitation, lipofection, particle bombardment, microinjection, electroporation, photoporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and in Ausubel et al. (2005, Current Protocols in Molecular Biology, John Wiley & Sons, New York). Thus, the invention encompasses expression vectors encoding a C-terminal MET receptor peptide or fusion protein of the invention, as well as cells comprising such vectors.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from baculovirus, papovavirus, vaccinia virus, pseudorabies virus, fowl pox virus, lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

In the case where a non-viral delivery system is utilized, a preferred delivery vehicle is a liposome. The above-mentioned delivery systems and protocols can be found in Gene Targeting Protocols, 2nd ed., Kmiec ed., Humana Press, Totowa, N.J., pp 1-35 (2002) and Gene Transfer and Expression Protocols, Vol. 7, (Methods in Molecular Biology) Murray ed., Humana Press, Totowa, N.J., pp 81-89 (1991).

Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Peptidomimetics

In some embodiments, the peptides disclosed herein can be modified according to the methods known in the art for producing peptidomimetics, See, e.g., Kazmierski, W. M., ed., Peptidomimetics Protocols, Human Press (Totowa N.J. 1998); Goodman et al., eds., Houben-Weyl Methods of Organic Chemistry: Synthesis of Peptides and Peptidomimetics, Thiele Verlag (New York 2003); and Mayo et al., J. Biol. Chem., 278:45746 (2003). In some cases, these modified peptidomimetic versions of the peptides and fragments disclosed herein exhibit enhanced stability in vivo, relative to the non-peptidomimetic peptides.

Methods for creating a peptidomimetic include substituting one or more, e.g., of the amino acids in a peptide sequence with D-amino acid enantiomers. Such sequences are referred to herein as "retro" sequences. In another method, the N-terminal to C-terminal order of the amino acid residues is reversed, such that the order of amino acid residues from the N terminus to the C terminus of the original peptide becomes the order of amino acid residues from the C-terminus to the N-terminus in the modified peptidomimetic. Such sequences can be referred to as "inverso" sequences.

Peptidomimetics can be both the retro and inverso versions, i.e., the "retro-inverso" version of a peptide disclosed herein. The new peptidomimetics can be composed of D-amino acids arranged so that the order of amino acid residues from the N-terminus to the C-terminus in the peptidomimetic corresponds to the order of amino acid residues from the C-terminus to the N-terminus in the original peptide.

Other methods for making a peptidomimetics include replacing one or more amino acid residues in a peptide with a chemically distinct but recognized functional analog of the amino acid, an artificial amino acid analog. Artificial amino acid analogs include beta-amino acids, beta-substituted beta-amino acids ("beta3-amino acids"), phosphorous analogs of amino acids, such as b-amino phosphonic acids and b-amino phosphinic acids, and amino acids having non-peptide linkages. Artificial amino acids can be used to create peptidonimetics, such as peptoid oligomers (e.g., peptoid amide or ester analogues), beta-peptides, cyclic peptides, oligourea or oligocarbamate peptides; or heterocyclic ring molecules.

Antibodies

In one embodiment, the peptides of the present invention may be used for the generation of an antibody. For example, one or more peptides of the invention may be used to generate an antibody that specifically binds to the peptide and therefore also to the C-terminus region of the MET receptor.

Methods of making and using antibodies are well known in the art. For example, polyclonal antibodies are generated by immunizing rabbits according to standard immunological techniques well-known in the art (see, e.g., Harlow et al., 1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that the antigenic protein of interest is rendered immunogenic (e.g., an antigen of interest conjugated with keyhole limpet hemocyanin, KLH) and a portion comprising the respective antigenic protein amino acid residues. In the present invention, the peptides of the invention may serve as the antigen. The chimeric proteins are produced by cloning the appropriate nucleic acids encoding the marker protein into a plasmid vector suitable for this purpose, such as but not limited to, pMAL-2 or pCMX.

The present invention should be construed to encompass antibodies which bind to the specific antigens of interest (i.e. C-terminus region of the MET receptor, and derivatives), and are able to bind the antigen present on Western blots, in solution in enzyme linked immunoassays, in fluorescence activated cells sorting (FACS) assays, in magenetic-actived cell sorting (MACS) assays, immunocytochemistry, immunoprecipitation, and in immunofluorescence microscopy of a cell transiently transfected with a nucleic acid encoding at least a portion of the antigenic protein, for example.

Once armed with the sequence of a specific antigen of interest and the detailed analysis localizing the various conserved and non-conserved domains of the protein, the skilled artisan would understand, based upon the disclosure provided herein, how to obtain antibodies specific for the various portions of the antigen using methods well-known in the art or to be developed.

Further, the skilled artisan, based upon the disclosure provided herein, would appreciate that using a non-conserved immunogenic portion can produce antibodies specific for the non-conserved region thereby producing antibodies that do not cross-react with other proteins which can share one or more conserved portions. Thus, one skilled in the art would appreciate, based upon the disclosure provided herein, that the non-conserved regions of an antigen of interest can be used to produce antibodies that are specific only for that antigenic peptide and do not cross-react non-specifically with other proteins or peptides.

The invention encompasses monoclonal, synthetic antibodies, and the like. One skilled in the art would understand, based upon the disclosure provided herein, that the crucial feature of the antibody of the invention is that the antibody bind specifically with an antigen of interest. That is, the antibody of the invention recognizes an antigen of interest or a fragment thereof (e.g., an immunogenic portion or antigenic determinant thereof), on Western blots, in immunostaining of cells, and immunoprecipitates the antigen using standard methods well-known in the art.

One skilled in the art would appreciate, based upon the disclosure provided herein, that the antibodies can be used to immunoprecipitate and/or immuno-affinity purify their cognate antigen as described in detail elsewhere herein, and additionally, by using methods well-known in the art.

The skilled artisan would appreciate, based upon the disclosure provided herein, that that present invention includes use of a single antibody recognizing a single antigenic epitope but that the invention is not limited to use of a single antibody. Instead, the invention encompasses use of at least one antibody where the antibodies can be directed to the same or different antigenic protein epitopes.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Therapeutic Methods

The C-terminal MET receptor peptides disclosed herein, or nucleic acids encoding the peptides, can be used to treat fibrosis. In several examples, the C-terminal MET receptor peptides, or nucleic acid encoding these peptides can be used to decrease fibrosis, such as in a subject. Thus, in several embodiments, the methods include administering to a subject a therapeutically effective amount of one or more of the peptides of the invention, or polynucleotides encoding these peptides, in order to decrease fibrosis. In some examples, the peptide comprises an amino acid sequence including but not limited to an amino acid sequence as set forth in SEQ ID NO: 1, SEQ ID NO: 2, SEQ ID NO: 3, SEQ ID NO: 4, SEQ ID NO: 5, SEQ ID NO: 6, SEQ ID NO: 7 or variants thereof.

In one embodiment, fibrosis includes the formation or development of excess fibrous connective tissue in an organ or tissue as a reparative or reactive process, as opposed to a formation of fibrous tissue as a normal constituent of an organ or tissue. Skin and lungs are susceptible to fibrosis. Exemplary fibrotic conditions are scleroderma idiopathic pulmonary fibrosis, morphea, fibrosis as a result of Graft-Versus-Host Disease (GVHD), keloid and hypertrophic scar, and subepithelial fibrosis, endomyocardial fibrosis, uterine fibrosis, myelofibrosis, retroperitoneal fibrosis, nephrogenic systemic fibrosis, scarring after surgery, asthma, cirrhosis/liver fibrosis, aberrant wound healing, glomerulonephritis, and multifocal fibrosclerosis.

In some instances, fibrotic diseases are characterized by the activation of fibroblasts, increased production of collagen and fibronectin, and transdifferentiation into contractile myofibroblasts. This process usually occurs over many months and years, and can lead to organ dysfunction or death. Examples of fibrotic diseases include diabetic nephropathy, liver cirrhosis, idiopathic pulmonary fibrosis, rheumatoid arthritis, atherosclerosis, cardiac fibrosis and scleroderma (systemic sclerosis; SSc). Fibrotic disease represents one of the largest groups of disorders for which there is no effective therapy and thus represents a major unmet medical need. Often the only redress for patients with fibrosis is organ transplantation; since the supply of organs is insufficient to meet the demand, patients often die while waiting to receive suitable organs. Lung fibrosis alone can be a major cause of death in scleroderma lung disease, idiopathic pulmonary fibrosis, radiation and chemotherapy-induced lung fibrosis and in conditions caused by occupational inhalation of dust particles.

The invention may be practiced in any subject diagnosed with, or at risk of developing, fibrosis. Fibrosis is associated with many diseases and disorders. Preferably, the fibrosis is idiopathic pulmonary fibrosis. The subject may be diagnosed with, or at risk for developing interstitial lung disease including idiopathic pulmonary fibrosis, scleroderma, radiation-induced pulmonary fibrosis, bleomycin lung, sarcoidosis, silicosis, familial pulmonary fibrosis, an autoimmune disease or any disorder wherein one or more fibroproliferative matrix molecule deposition, enhanced pathological collagen accumulation, apoptosis and alveolar septal rupture with honeycombing occurs. The subject may be identified as having fibrosis or being at risk for developing fibrosis because of exposure to asbestos, ground stone and metal dust, or because of the administration of a medication, such as bleomycin, busulfon, pheytoin, and nitro furantoin, which are risk factors for developing fibrosis. Preferably, the subject is a mammal and more preferably, a human. It is also contemplated that the compositions and methods of the invention may be used in the treatment of organ fibrosis secondary to allogenic organ transplant, e.g., graft transplant fibrosis. Non-limiting examples include renal transplant fibrosis, heart transplant fibrosis, liver transplant fibrosis, etc.

In certain embodiments, the methods of the present invention are used to treat multiple fibrotic diseases with underlying causes including myocardial infarct, cirrhosis, hepatitis, etc.

The invention may be practiced in any subject diagnosed with, or at risk of developing, scleroderma. Scleroderma is a chronic autoimmune disease characterized by fibrosis (or hardening), vascular alterations, and autoantibodies. There are two major forms: limited systemic scleroderma and diffuse systemic scleroderma. The cutaneous symptoms of limited systemic scleroderma affect the hands, arms and face. Patients with this form of scleroderma frequently have one or more of the following complications: calcinosis, Raynaud's phenomenon, esophageal dysfunction, sclerodactyl), and telangiectasias.

Diffuse systemic scleroderma is rapidly progressing and affects a large area of the skin and one or more internal organs, frequently the kidneys, esophagus, heart and/or lungs.

Scleroderma affects the small blood vessels known as arterioles, in all organs. First, the endothelial cells of the arteriole die off apoptotically, along with smooth muscle cells. These cells are replaced by collagen and other fibrous material. Inflammatory cells, particularly CD4+ helper T cells, infiltrate the arteriole, and cause further damage.

The skin manifestations of scleroderma can be painful, can impair use of the affected area (e.g., use of the hands, fingers, toes, feet, etc.) and can be disfiguring. Skin ulceration may occur, and such ulcers may be prone to infection or even gangrene. The ulcerated skin may be difficult or slow to heal. Difficulty in healing skin ulcerations may be particularly exacerbated in patients with impaired circulation, such as those with Raynaud's phenomenon. In certain embodiments, the methods of the present disclosure are used to treat scleroderma, for example skin symptoms of scleroderma. In certain embodiments, treating scleroderma comprises treating skin ulceration, such as digital ulcers. Administration of the peptides of the invention can be used to reduce the fibrotic and/or inflammatory symptoms of scleroderma in affected tissue and/or organs.

In addition to skin symptoms/manifestations, scleroderma may also affect the heart, kidney, lungs, joints, and digestive tract. In certain embodiments, treating scleroderma includes treating symptoms of the disease in any one or more of these tissues, such as by reducing fibrotic and/or inflammatory symptoms.

Lung problems are amongst the most serious complications of scleroderma and are responsible for much of the mortality associated with the disease. The two predominant lung conditions associated with scleroderma are pulmonary fibrosis and pulmonary hypertension. A patient with lung involvement may have either or both conditions. Lung fibrosis associated with scleroderma is one example of pulmonary fibrosis that can be treated using the peptides of the invention.

Scleroderma involving the lung causes scarring (pulmonary fibrosis). Such pulmonary fibrosis occurs in about 70% of scleroderma patients, although its progression is typically slow and symptoms vary widely across patients in terms of severity. For patients that do have symptoms associated with pulmonary fibrosis, the symptoms include a dry cough, shortness of breath, and reduced ability to exercise. About 16% of patients with some level of pulmonary fibrosis develop severe pulmonary fibrosis. Patients with severe pulmonary fibrosis experience significant decline in lung function and alveolitis.

In certain embodiments, the methods of the present invention include the use of the peptides of the invention to treat scleroderma, for example lung fibrosis associated with scleroderma. Administration of the peptides of the invention can be used to reduce the fibrotic symptoms of scleroderma in lung. For example, the methods can be used to improve lung function and/or to reduce the risk of death due to scleroderma. For example, the peptides of the invention can be used to treat scleroderma associated interstitial lung disease.

Kidney involvement is also common in scleroderma patients. Renal fibrosis associated with scleroderma is an example of renal fibrosis that can be treated by administration of a peptide of the invention.

In certain embodiments, the methods of the present invention are used to treat scleroderma, for example kidney fibrosis associated with scleroderma. Administration of a peptide of the invention can be used to reduce the fibrotic symptoms of scleroderma in kidney. For example, the methods can be used to improve kidney function, to reduce protein in the urine, to reduce hypertension, and/or to reduce the risk of renal crisis that may lead to fatal renal failure.

In certain embodiments, methods of treating scleroderma include administering a peptide of the invention as part of a therapeutic regimen along with one or more other drugs, biologics, or therapeutic interventions appropriate for scleroderma. In certain embodiments, the additional drug, biologic, or therapeutic intervention is appropriate for particular symptoms associated with scleroderma. By way of example, a peptide of the invention may be administered as part of a therapeutic regimen along with one or more immunosuppressive agents, such as methotrexate, cyclophosphamide, azathioprine, and mycophenolate mofetil. By way of further example, a peptide of the invention may be administered as part of a therapeutic regimen along with one or more agents designed to increase blood flow, such as blood flow to ulcerated digits (e.g., nifedipine, amlodipine, diltiazem, felodipine, or nicardipine). By way of further example, a peptide of the invention may be administered as part of a therapeutic regimen along with one or more agents intended to decrease fibrosis of the skin, such as d-penicillamine, colchicine, PUVA, Relaxin, and cyclosporine. By way of further example, a peptide of the invention may be administered as part of a therapeutic regimen along with steroids or broncho-dilators.

Moreover, methods of treatment may include a treatment regimen including a dietary regimen, an exercise regimen, stress management, smoking cessation, acupuncture, massage, and/or physical therapy.

Pharmaceutical Compositions

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts.

Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Other active agents useful in the treatment of fibrosis include anti-inflammatories, including corticosteroids, and immunosuppressants.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

Cosmetic Composition

A final product of wound healing is a scar. Collagen remodeling during scar formation is dependent on both continued collagen synthesis and collagen catabolism. Delays in the healing process cause the prolonged presence of wounds, while abnormalities of the healing process may lead to abnormal scar formation. Successful completion of wound healing may not always yield the desired clinical result, particularly where the final cosmetic appearance of the scar is of primary importance. Therefore, the peptides of the present invention also have an application as cosmetic compositions, e.g. for use to reduce the appearance of scars.

The formulations of the cosmetic compositions described herein may be prepared by any method known or hereafter developed in the art. The peptides of the present invention can be formulated in various cosmetic consumer products utilizing a variety of delivery systems and carrier bases. Such consumer product forms include the group consisting of lotions, skin creams, band-aids, and balms.

In another aspect, the delivery system or a carrier base are selected in the form of a lotion, cream, gel, spray, thin liquid, powder, compressed powder, paste, salve, collodion, and similar delivery or packaging form.

In another aspect, the delivery system can be traditional water and oil emulsions, suspensions, colloids, microemulsions, clear solutions, suspensions of nanoparticles, emulsions of nanoparticles, or anhydrous compositions.

Additional cosmetically beneficial ingredients can also be included in the formulated compositions of the present invention, which can be selected from, but not limited to skin cleansers, cationic, anionic surfactants, non-ionic surfactants, amphoteric surfactants, and zwitterionic surfactants, skin and hair conditioning agents, vitamins, hormones, minerals, plant extracts, anti-inflammatory agents, collagen and elastin synthesis boosters, UVA/UVB sunscreens, concentrates of plant extracts, emollients, moisturizers, skin protectants, humectants, silicones, skin soothing ingredients, antimicrobial agents, antifungal agents, treatment of skin infections and lesions, blood microcirculation improvement, skin redness reduction benefits, additional moisture absorbents, analgesics, skin penetration enhancers, solubilizers, moisturizers, emollients, anesthetics, colorants, perfumes, preservatives, seeds, broken seed nut shells, silica, clays, beads, luffa particles, polyethylene balls, mica, pH adjusters, processing aids, and combinations thereof.

In another preferred aspect, the cosmetically acceptable composition further comprises one or more excipient. Exemplary excipients include, but are not limited to water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about Cm to C22, long chain fatty amines from about Cm to C22, fatty alcohols, ethoxylated fatty alcohols and di-tail phospholipids.

Diagnosis

In one embodiment, the invention provides a method of diagnosing a subject with a disease or disorder associated with dysfunctional cleavage of the c-MET receptor tyrosine kinase. For example, the D1398G MET receptor mutant does not exert any of MET's anti-fibrotic effects in lung fibroblasts. Thus, subjects identified having this mutant would be candidates for receiving the peptides and compositions of the invention. Alternatively, subjects identified as having the D1398G MET receptor mutant can receive any c-MET protein therapy.

Accordingly, the D1398G MET receptor mutant is a biomarker for a disease or disorder associated with dysfunctional cleavage of the c-MET receptor tyrosine kinase. The biomarker of the invention can be used to facilitate the optimum selection of treatment protocols, and open new venues for the development of effective therapy for fibrosis. Biomarkers of the invention can be used to guide treatment selection for individual patients, as well as to guide the development of new therapies specific to each type of fibrosis.

Kits

The present invention also pertains to kits useful in the methods of the invention. In one embodiment of the invention, the kit comprises components for diagnosing a disease or disorder associated with dysfunctional cleavage of the c-MET receptor tyrosine kinase in a subject as elsewhere described herein. Such kits comprise components useful in any of the methods described herein, including for example, hybridization probes or primers (e.g., labeled probes or primers), reagents for detection of labeled molecules, oligonucleotide arrays, restriction enzymes, antibodies, allele-specific oligonucleotides, means for amplification of a subject's nucleic acids, means for reverse transcribing a subject's RNA, means for analyzing a subject's nucleic acid sequence, and instructional materials. For example, in one embodiment, the kit comprises components useful for the detection of the D1398G MET mutation in a genomic DNA sample from a subject. In one embodiment the kit comprises components useful for the detection of the D1398G MET mutation in a RNA sample from a subject.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Identification of D1389G Variant of MET Receptor Tyrosine Kinase

Caspase-3 plays a key effector role in apoptosis by cleaving specific substrates important for downstream apoptosis signaling (Slee, et al., J Biol Chem, 2001, 276(10): 7320-6) and has some additional functions including B cell regulation and T cell differentiation (Woo, et al., Nat Immunol, 2003, 4(10):1016-22 and De Botton, et al., Blood, 2002, 100(4):1310-7). An autoantibody against caspase-3 is generated in SSc, and this antibody has been correlated to the severity of SSc-ILD, vascular damage, and inflammation (Okazaki, et al., Rheumatol Int, 2010, 30(7):871-8). Activated caspase-3 recognizes aspartic acid-containing motifs within MET and cleaves those generating several stable fragments of the MET receptor that have been implicated in regulation of cell apoptosis and MET expression (Lefebvre, et al., Cell Death Dis, 2013, 4:e871 and Ma, et al., Hepatology, 2014, 59(5):2010-21). Upon cleavage by caspase-3, the intracellular cytoplasmic tail of MET generates a 10 amino acid peptide, TRPASFWETS (SEQ ID NO:1), designated as "M10".

The materials and methods are now described

Lung Tissue and Cell Culture

Lung tissues were collected postmortem from three SSc patients who fulfilled the 2013 ACR/EULAR classification criteria for SSc (Van den Hoogen, et al., Arthritis Rheum, 2013, 65:2737-47) and had evidence of lung involvement according to guidelines of the IRB of the Medical University of South Carolina (MUSC). The diagnosis of SSc-ILD was confirmed by histological examination of postmortem lung tissue. Lung fibroblasts were isolated from scleroderma lung tissue and from age-, race-, and sex-matched controls as previously described (Bogatkevich, et al., J Biol Chem, 2001, 276: 45184-92) and used between second and fourth passages in all experiments. Human fetal lung fibroblasts MRC5 were purchased from Sigma, human lung adenocarcinoma epithelial cells A549 were purchased from Lonza (Walkersville, Md.).

Generation of Recombinant MET Wild Type and MET D1398G Adenovirus Plasmids

The wild type (WT) full-length c-MET cDNA in pLXSN was a generous gift from Dr. Morag Park, McGill University, Montreal, Canada. The Quik Change Lightning Multi Site-Directed Mutagenesis Kit (Agilent technologies) was used to generate MET D1398G mutant using forward primer GAAGATAACGCTGATGATGAGGTGGGCACACGAC-CAG (SEQ ID NO: 8) and reverse primer CTGGTCGTGT-GCCCACCTCATCATCAGCGTTATCTTC (SEQ ID NO: 9). Xho-I and Hind-III were used to digest pLXSN+MET construct followed by subcloning of MET WT and MET D1398G into pAdTrack-CMV vector and digestion with Pac-I. The linearized plasmids were amplified in 293A cells according to the manual for the AdEasy system (Stratagene, La Jolla, Calif.) and purified by double CsCl gradient ultracentrifugation. The titer, cytopathic effects and function of MET WT and MET D1398G recombinant adenoviruses were determined followed by adjusting virus particle per cell in both lung fibroblasts and alveolar epithelial cells. Western blots and immunofluorescent staining were routinely performed to monitor expression level changes of MET between infected and uninfected cells.

Immunohistochemistry

Lung tissues were washed with PBS, fixed in 4% paraformaldehyde, and embedded in paraffin blocks. Seven μm paraffin sections were collected on slides, deparaffinized in histo-clear, and rehydrated through a degrading series of ethanol before staining. Antigen retrieval was performed by Antigen Unmasking solution (Vector Laboratories) and permeabilized for 10 minutes in 0.1% Triton X-100. Nonspecific binding sites were blocked for 40 minutes in Background Buster (Innova Biosciences). The slides were immunostained with anti-MET C12 from Santa Cruz Biotechnology and anti-MET 4F8.2 from Millipore. Fluorescence signals were visualized with a Leica DMI4000B fluorescence microscope equipped with Hamamatsu Camera Controller ORCA-ER and quantified by Adobe Photoshop CS3 software using the Count Tool. Cells stained positively for MET were counted using at least six none-overlapping high-power fields at ×400 magnification per sample. The results are presented as a percentage of positive cells over total nucleated cells.

Caspase 3 Assay

Caspase 3 Assay Kit (Abcam, Cambridge, Mass.) was used to detect apoptosis in cultured cells. The cells were plated on 100 mm plates, transfected with MET WT or D1398G, and treated with or without FasL and cisplatin for 24 h. Cell lysates were collected in accordance to with the manufacturer's instructions, transferred to a 96-well plate, and incubated with DEVD-p-NA substrate at 37° C. for 2 hours followed by reading the absorbance at 405 nm on a spectrophotometer.

Ras Activity Assay

G-LISA Kit (Cytoskeleton Inc., Denver, Colo.) was used to measure endogenous Ras-GTP levels. Cells were plated on 100 mm plates, transfected with MET WT or variant D1398G, treated with or without HGF for 24 h, and subjected to the assay in accordance with the manufacturer's instructions. Bound Ras-GTP levels were determined by anti-Ras primary antibody followed by horseradish peroxidase-conjugated secondary antibody. A peroxidase substrate was applied, and the plates were read at 450 nm on a spectrophotometer.

Preparation of Cell Extracts and Immunoblotting

Cells were collected and analyzed by immunoblotting as previously described (Bogatkevich et al., J Biol Chem. 2001, 276:45184-45192; Bogatkevich et al., Arthritis Rheum. 2007, 56:3468-3477). Phosphorylation of MET was analyzed using anti-phospho-c-Met [pYpYpY$^{1230/1234/1235}$], pY$^{1349}$, and pY$^{1356}$ antibodies (BioSource International, Inc., Camarillo, Calif.). Total MET was immunobloted using anti-MET (C12) (Santa Cruz Biotechnology, Santa Cruz, Calif.) and anti-MET (25H2) (Cell Signaling, Danvers, Mass.). Anti-type I collagen antibody (Southern Biotechnology, Birmingham, Ala.)), anti-CTGF antibody (Santa Cruz Biotechnology, Santa Cruz, Calif.), and anti-smooth-α-actin antibody (Sigma, St. Louis, Mo.) were also used.

The phosphorylation of p42/p44 MAPK isoforms was analyzed using anti-phospho-Erk1/2 and Erk1/2 antibodies in accordance with the manufacturer's instructions (Cell Signaling Technology, Danvers, Mass.). Immunoblots were routinely stripped and reblotted with anti-β-actin antibody (Sigma, St. Louis, Mo.) as a loading control.

Statistical Analysis

Statistical analyses were performed with KaleidaGraph 4.0 (Synergy Software, Reading, Pa.). All data were analyzed using ANOVA with post-hoc testing.

The results were considered significant if $p<0.05$.

The results of the experiments are now described.

Identification of a D1398G Gene Variant in Scleroderma Patients and Generation D1398G Adenovirus A MET gene variant at position 1398 with aspartic acid (D) substituted by glycine (G), D1398G, was identified in some scleroderma lung fibroblasts (SSc LF) with defective HGF signaling, described in previous publications (Bogatkevich, et al., Arthritis Rheum, 2007, 56:2432-42 and Bogatkevich, et al., Arthritis Rheum, 2007, 56:3468-77). The frequency of the D1398G variant in scleroderma patients is currently under investigation (Atanelishvili, et al., Arthritis Rheum, 2013, 65(10 Suppl.), 2907). The following studies were undertaken to elucidate the effect of a D1398G mutation and its potential role in the pathogenesis of SSc-ILD.

Using site-directed mutagenesis, a D1398G mutant was constructed, followed by generation of adenoviruses containing either MET wild type (WT) or MET D1398G mutant. Transfection of LF and AEC was adjusted to contain 10 to 12 adenoviruses per one cell. Expression of MET WT and MET D1398G mutant was routinely monitored by immunoblotting and immunofluorescent staining.

MET Phosphorylation in LF and AEC Transfected with MET WT and MET D1398G

As an initial approach to evaluate the functional consequences of D1398G mutation, HGF-induced MET autophosphorylation was studied in LF and AEC (A549 cell line) transfected either with MET WT or D1398G mutant. MET tyrosine phosphorylation was assessed using anti-phospho-c-Met[pYpYpY$^{1230/1234/1235}$], pY$^{1349}$, and pY$^{1356}$ antibodies. Treatment with HGF induced rapid phosphorylation of MET WT at tyrosine 1230, 1234, and 1235 in both LF and AEC. Maximal phosphorylation was observed within 5 minutes of HGF treatment and decreased by 20 minutes following HGF treatment (FIG. 1). HGF-induced phosphorylation at tyrosine 1349 appeared to take place after tyrosine 1230, 1234, and 1235 phosphorylation with maximal levels observed between 20 minutes and 1 hour. The time course of HGF-induced phosphorylation at tyrosine 1356 in LF resembled tyrosine 1230, 1234, and 1235 phosphorylation with maximal levels observed within 5 minutes of HGF treatment. Tyrosine 1356 phosphorylation in AEC appeared to be stronger than in LF with maximal levels observed within 20 minutes of HGF treatment. In contrast to MET WT, tyrosine phosphorylation of MET D1398G was decreased and delayed in both LF and AEC. Thus, HGF-induced phosphorylation of MET D1398G at tyrosine 1356 was visibly reduced, not reaching its maximal value until 1 hour as compared to 5 minutes for MET WT in LF and 20 minutes in AEC.

Figures 2A, 2B:
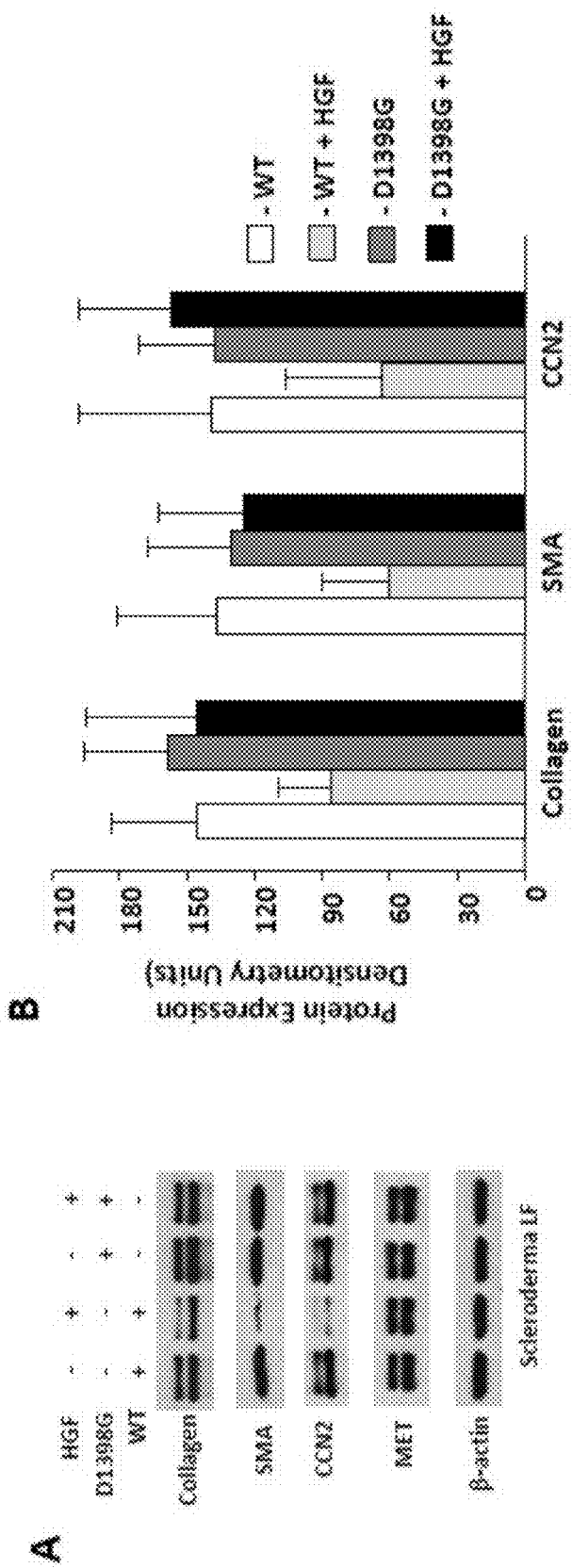
FIG. 2A and FIG. 2B, depicts Expression of type I collagen, SMA, and CCN2 in scleroderma lung fibroblasts (LF) transfected with MET WT and MET D1398G.
Figures 3A, 3B, 3C, 3D:
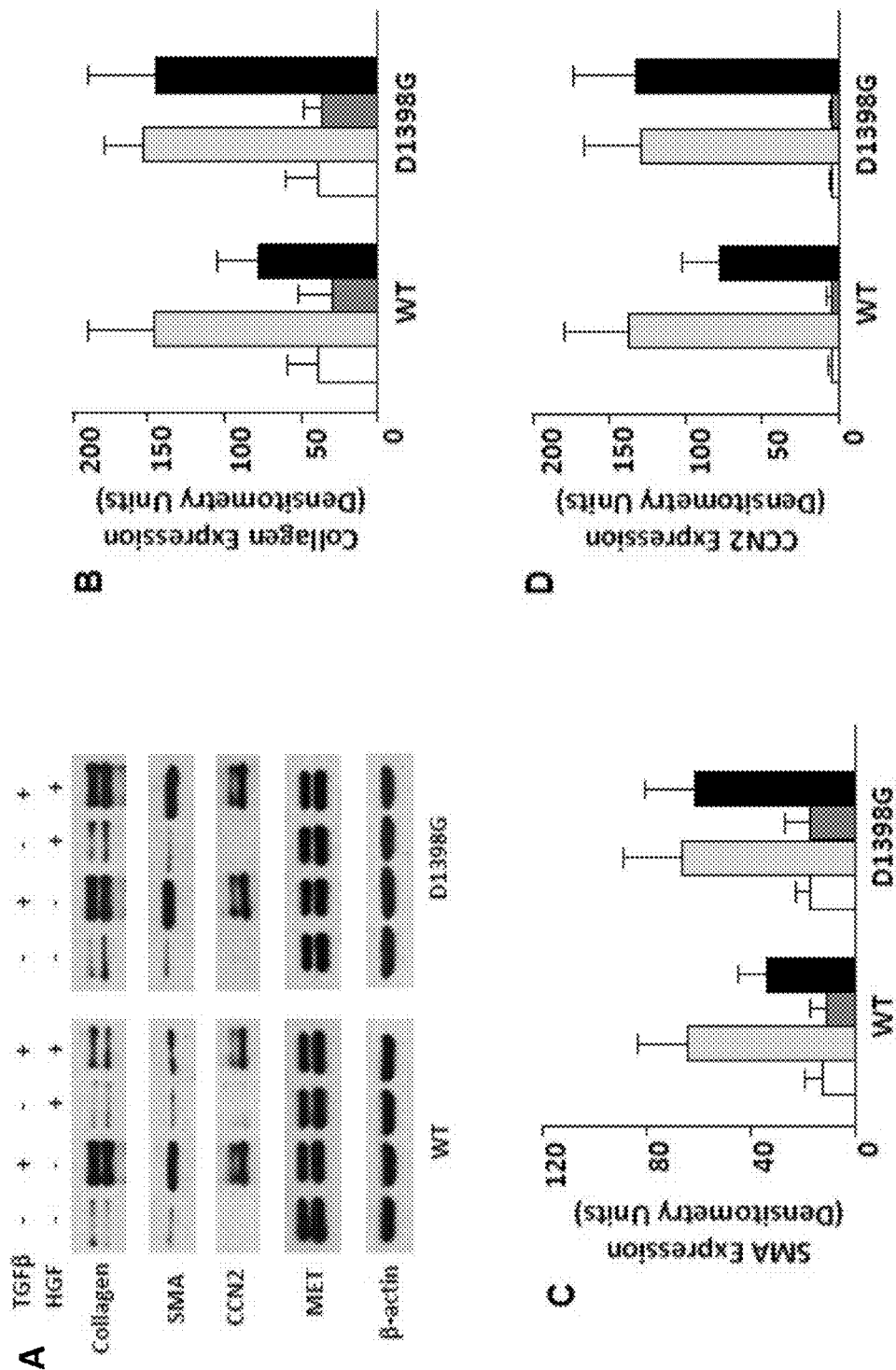
FIG. 3A through FIG. 3D, depicts expression of type I collagen, SMA, and CCN2 in normal lung fibroblasts (LF) transfected with MET WT and MET D1398G. Transfected SSc lung fibroblasts were serum-starved for 24 hours followed by incubation for 48 hours with recombinant TGFβ (5 ng/ml) and/or HGF (50 ng/ml).

Effects of HGF on Collagen, SMA, and CTGF in Scleroderma and Normal Lung Fibroblasts Transfected with MET WT and MET D1398G Scleroderma LF transfected with the D1398G mutant or with the MET WT expressed similar basal levels of collagen, SMA, and CTGF. HGF, when added to cell culture medium at a concentration of 50 ng/ml for 48 hours, led to reduced expression of collagen, SMA, and CTGF only in LF transfected with MET WT, and not in LF transfected with mutant MET D1398G (FIG. 2). To investigate the effect in normal LF, cells transfected with MET WT and mutant D1398G were pre-incubated with TGFβ followed by incubation with HGF for 48 hours. In normal LF, basal and TGFβ-induced collagen, SMA and CTGF were indistinguishable between cells transfected with MET WT and mutant D1398G. HGF, however, decreased the levels of collagen, SMA and CTGF in TGFβ-stimulated normal LF transfected with MET WT but not in TGFβ-stimulated normal LF transfected with MET D1398G (FIG. 3).

HGF-Induced Activation of Ras and MAPK in LF and AEC Transfected with MET WT and MET D1398G It has been previously demonstrated that HGF-induced down regulation of collagen and CTGF in scleroderma LF is mediated by a MAPK-dependent pathway (Bogatkevich, et al., Arthritis Rheum, 2007, 56:3468-77). To investigate whether the D1398G mutation affects MAPK signaling pathways, the Erk1/2 phosphorylation was examined. Basal and HGF-induced Erk1/2 phosphorylation were more prominent in AEC as compared with LF. HGF further induced Erk1/2 phosphorylation in LF and AEC transfected either with MET WT or with MET D1398G. HGF-induced Erk1/2 phosphorylation in cells transfected with MET WT was notably higher as compared with cells transfected with MET D1398G (FIGS. 4 A and B). The basal level of nonphosphorylated Erk1/2 in LF and AEC was not affected either by HGF stimulation or by transfection with D1398G mutation.

Figures 4A, 4B, 4C, 4D:
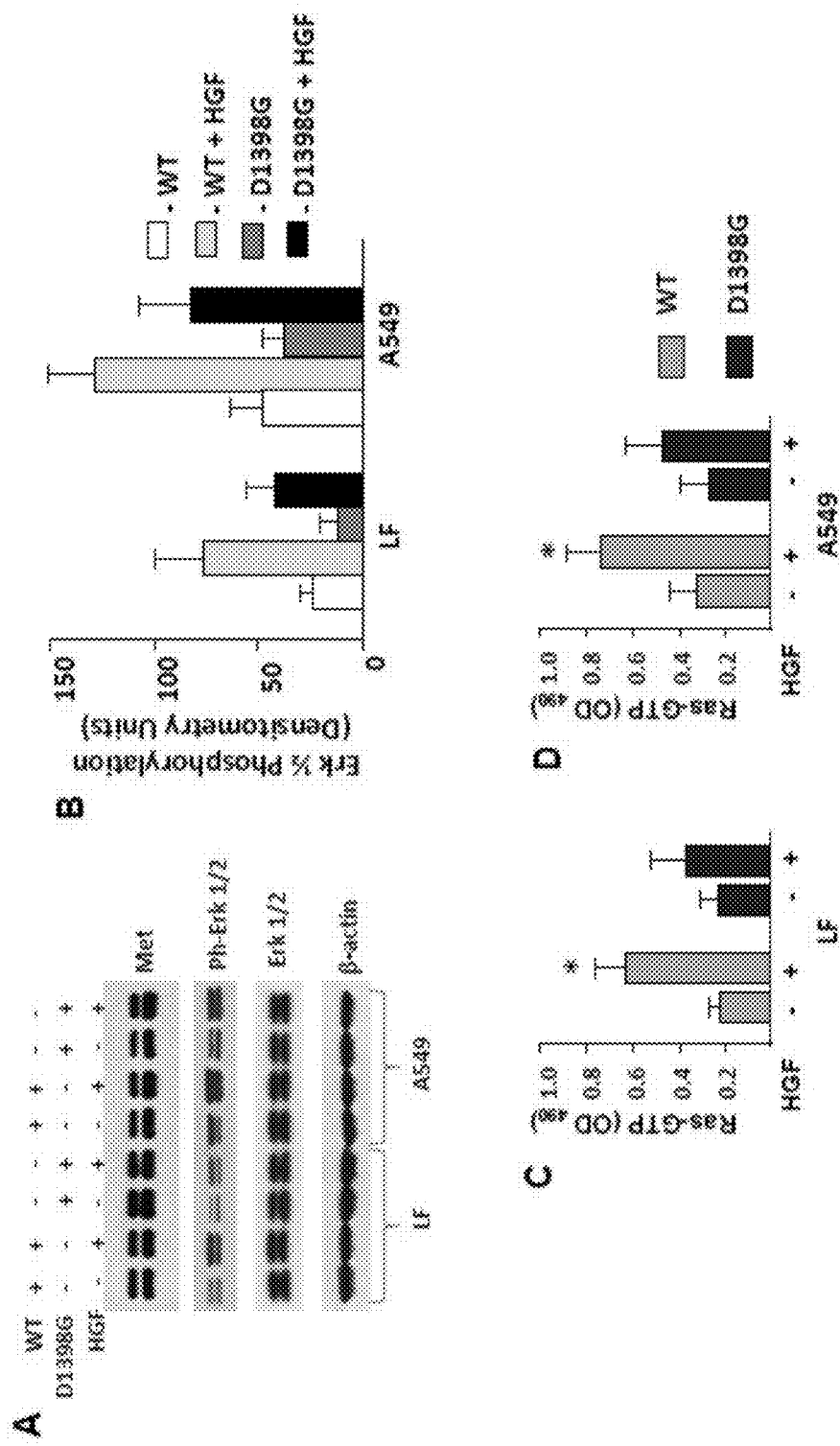
FIG. 4A through FIG. 4D, depicts the effect of HGF on Ras activation and Erk1/2 phosphorylation in lung fibroblasts (LF) and alveolar epithelial cells (AEC).

HGF-induced phosphorylation of Erk1/2 is mediated by Ras (Campbell, et al., Oncogene, 1998, 17:1395-413). To investigate whether D1398G mutation affects MET-dependent Ras activation, Ras-GTP in LF and in AEC transfected with MET WT and with MET D1398G was measured. A significant increase in total Ras activity in the presence of HGF in both LF and AEC transfected with MET WT was observed, but not in either cell type transfected with MET D1398G (FIGS. 4C and 4D).

D1398G Prevents Caspase-3 Cleavage of the C-Terminal Portion of MET

Figures 5A, 5B:
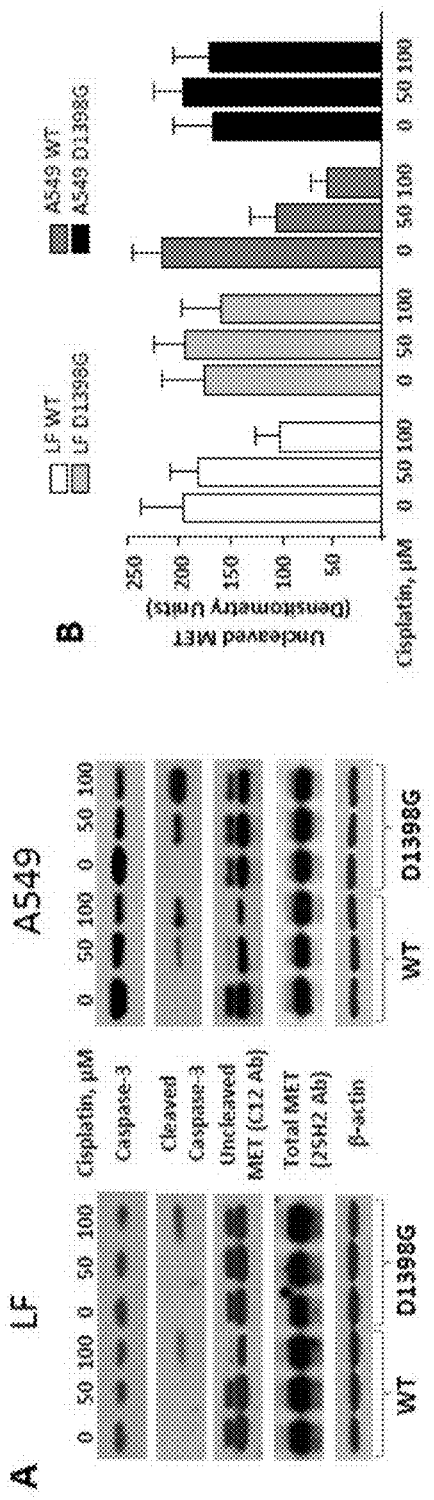
FIG. 5A and FIG. 5B, depicts effects of cisplatin in lung fibroblasts (LF) and alveolar epithelial cells (AEC) transfected with MET WT and MET D1398G.

Aspartic acid at position 1398 is the terminal amino acid of the caspase-3 cleavage motif, DEVD-T, at the C-terminus of MET. To induce caspase-3 in cells, the caspase-3-activator cisplatin was used. AEC was found to be more sensitive to cisplatin treatment than LF. In fact, cleaved or active caspase-3 was detectable by Western blot in AEC but not in LF incubated with 50 μM cisplatin for 24 h. Further increases of cisplatin concentration (to 100 μM) yielded cleaved caspase not only in AEC but also in LF (FIG. 5). To investigate whether caspase-3 cleaves the C-terminal part of MET in AEC and LF, various anti-MET antibodies were employed that were generated against different parts of MET: C12 antibody was generated against the terminal 12 amino acids of MET, and 25H2 antibody was generated against the kinase domain of MET. Cisplatin-induced caspase-3 cleavage was associated with a loss of detectable MET protein in Western blots with the C12 antibody, suggesting that activated caspase-3 cleaves MET at position 1398. If TRPASFWETS (SEQ ID NO: 1), the terminal 10 amino acids of MET, referred to as "M10", are removed then C12 antibody no longer recognizes MET, resulting in decreased concentration of MET on Western blots. In contrast, under the same conditions MET protein levels detected by 25H2 antibody remain unchanged suggesting that C12 immunoblotting reflects loss of MET C-terminus but not the entire protein. Importantly, there was no difference in MET protein levels between C12 and 25H2 immunoblots of LF and AEC transfected with the D1398G mutant and incubated with and without cisplatin, thus indicating that caspase-3 is not able to recognize and cleave the DEVG-T motif.

MET in Lung Tissues Isolated from Patients with SSc-ILD

Figures 6A, 6B, 6C, 6D:
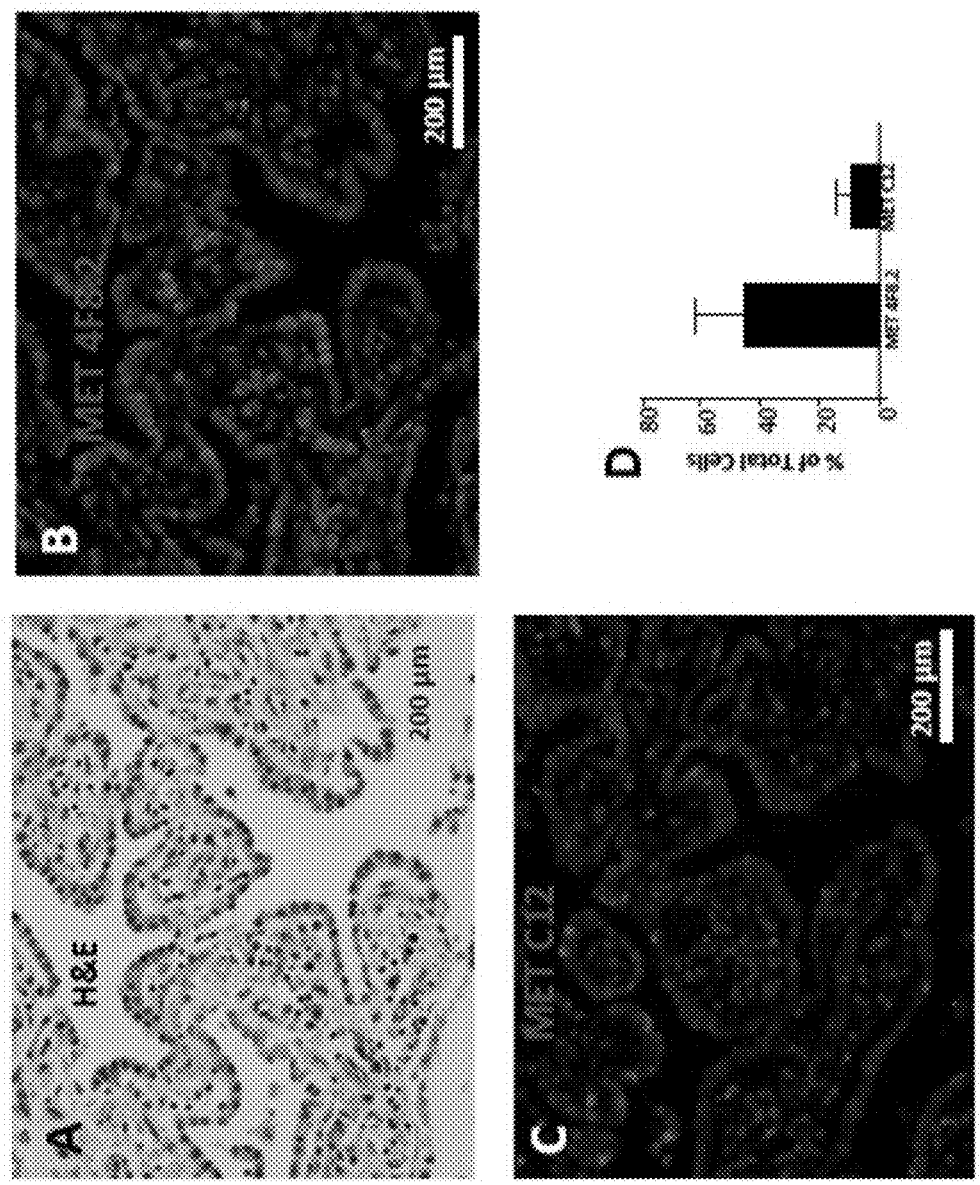
FIG. 6A through FIG. 6D, depicts expression of MET in lung tissues of patients with SSc-ILD.

To investigate whether loss of the MET C-terminus occurs in patients with SSc-ILD, immunofluorescent staining of lung tissues with C12 antibody and with anti-MET 4F8.2 antibody generated against the MET extracellular domain was performed. Lung tissues isolated from three different patients who died from end-stage SSc-ILD was examined. Hematoxylin and eosin staining of each sample demonstrated severe disarrangement of lung architecture with thickened alveolar septae and residual air spaces (FIG. 6). In immunohistochemial studies, 44.5±18.2% of cells in fibrotic lung tissues expressed MET as indicated by positive immunofluorescent signal with the 4F8.2 antibody. In contrast, only 9.1±6.7% of total lung cells express the C-terminal portion of MET, suggesting that cleavage and loss of the MET C-terminus occurred in these SSc-ILD patients.

D1398G Mutation Interferes with Anti-Apoptotic Effects of MET in AEC

Figure 7:
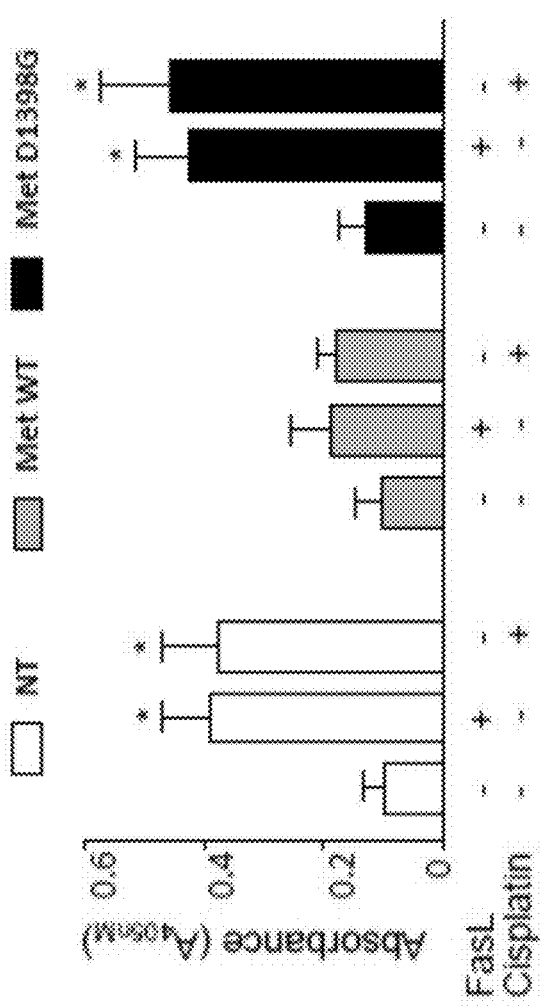
FIG. 7 depicts alveolar epithelial cells (AEC) transfected with MET WT but not with MET D1398G are protected from FasL- and cisplatin-induced apoptosis. Transfected AEC were incubated with or without FasL or cisplatin for 24 hours, collected with lysis buffer and analyzed by Caspase 3 Assay as detailed in Materials and Methods. Each bar represents mean and SD of duplicate determinations in three experiments. *Statistically significant differences FasL- and cisplatin-treated versus untreated cells, p<0.01.

A cell-protective effect of HGF and MET have been reported in AEC in numerous studies (Crestani, et al., Proc Am Thorac Soc, 2012, 9(3):158-63 and Gazdhar, et al., Hum Gene Ther, 2013, 24(1):105-16). To investigate if the D1398G mutation interferes with anti-apoptotic effects of MET in AEC, apoptosis of AEC with FasL and cisplatin and measured caspase 3 activity in cell lysates was induced. Incubation of AEC for 24 h with either FasL or cisplatin resulted in apoptosis reflected by an increase in the level of active caspase 3 (FIG. 7). Transfection of AEC with MET WT significantly reduced apoptosis decreasing FasL- and cisplatin-induced caspase (2.1- and 2.2-fold, respectively; $p<0.01$). In contrast, AEC transfected with the MET D1398G mutant were not protected from FasL- and cisplatin-induced apoptosis.

Example 2: Identification of Novel Anti-Fibrotic Peptide in C-Terminal Region of the MET Receptor Tyrosine Kinase Small peptides are widely involved in multiple cellular events and play very important roles in various cell functions. Interest in peptides as potential drug candidates remains high. With advances in such fields as chemical synthesis and peptide formulation, peptide drugs—especially short synthetic and long-acting peptides—are quickly increasing in the global market (Fonseca, et al., Adv Drug Deliv Rev, 2009, 61:953-64). The advantages of small peptides as drugs include their high biological activity, high specificity, and low toxicity (Craik et al., Chem Biol Drug Des. 2013, 81:136-147). Highly effective treatment for scleroderma-associated pulmonary fibrosis and other important fibrosing diseases is lacking, which makes identification of a peptide with antifibrotic properties a potentially very exciting and important discovery for this and other fibrosing diseases.

A small 10-amino acid peptide, "M10", is derived from the C-terminal part of the MET receptor tyrosine kinase via naturally occurring caspase-3 mediated cleavage (Atanelishvili, et al., Arthritis Rheum, 2013, 65(10 Suppl.), 2907). MET can generate M10 without HGF stimulation and that the MET D1398G mutant is incapable of generating M10, as aspartic acid at position 1398 is necessary for caspase-3 cleavage (Atanelishvili, et al., Arthritis Rheum, 2013, 65(10 Suppl.), 2907). The present study was designed to investigate the antifibrotic effects of M10 in lung and skin fibroblasts isolated from SSc patients.

Without being bound to a particular theory, because M10 is an intracellular fragment of MET, it was hypothesized that its primary effects would be exerted inside of cells. Trans-location of peptides through the cell membrane in general can occur via endocytosis or through direct diffusion in an energy-independent manner mediated by membrane potential (Choi and David, Curr Pharm Biotechnol. 2014, 15:192-199). M10 is a 10-mer peptide containing at its N-terminus the uncharged amino acid proline directly following a cationic amino acid arginine, which favors the transport of the peptide through membranes (Fonseca, et al., Adv Drug Deliv Rev, 2009, 61:953-64). This composition of amino acids within M10 suggests that the peptide can easily penetrate the lipid bilayers not only of the cell membrane but also of the nuclear membrane. In agreement with this, using immunofluorescence, M10 was observed in cytoplasm and nuclei of fibroblasts. Because the C12 antibody used in these experiments can recognize not only M10 but also uncleaved MET, direct coupling of M10 to a fluorophore (5,6-TAMRA) was also used to evaluate the distribution of M10 in fibroblasts. Patterns of M10 localization within cells were identical when detected by the fluorescent signals generated by C12 antibody or by those produced by the fluorophore 5,6-TAMRA, which suggests that M10's intracellular location can be either intracytoplasmic or intranuclear.

Excessive expression of collagen is a hallmark of scleroderma and other fibrotic diseases, and TGFβ is the main fibrogenic cytokine stimulating production of collagen in fibroblasts (Varga and Whitfield, Front Biosci (Schol Ed), 2009, 1:226-235). Therefore, synthetic M10 was tested for its effect on collagen expression in lung and skin fibroblasts isolated from SSc patients and in TGFβ-stimulated normal lung and skin fibroblasts. M10 diminished collagen in SSc lung and skin fibroblasts in vitro. Importantly, M10 reduced TGFβ-induced collagen type I in normal fibroblast and had no effects on basal levels of collagen, which suggests that M10 interferes with TGFβ-dependent fibrogenic pathways in fibroblasts.

TGFβ signaling in fibroblasts plays a major pathogenic role in SSc and other fibrosing diseases. Most of TGFβ-induced signal transduction is mediated intracellularly by Smad proteins, including receptor-regulated (R) Smads (Smad2 and Smad3), common (Co) Smad (Smad4), and inhibitory (I) Smads (Smad6 and Smad7). Smads are intracellular proteins that act as transcription factors to regulate gene expression (Hill, Int J Biochem Cell Biol. 1999, 31:1249-1254). They consist of a conserved N-terminal MH1 domain and a C-terminal MH2 domain connected by a linker region (Hill, Int J Biochem Cell Biol. 1999, 31:1249-1254). The MH2 domain can interact with a diverse group of proteins including membrane anchoring proteins and transcription factors (Chacho et al., Mol Cell, 2004, 15:813-823).

Peptide-mediated interactions, in which a short linear motif binds to a globular domain, play major roles in many biological processes, such as protein localization, endocytosis, post-translational modifications, and signal transduction (London et al., Structure, 2010, 18:189-199). Using computational modulation, the MH2 domain of Smad2 protein was found to interact with the M10 peptide. Herein, this was confirmed by protein interaction and coimmunoprecipitation experiments. In addition, using immunofluorescent studies, M10 was shown to colocalize with Smad2 in cytoplasm and in nuclei in the presence of TGFβ. Without being bound to a particular theory, these experiments suggest that the M10:Smad2 interaction is quite persistent and might be involved in the regulation of Smad2 functions.

In addition to the peptide interaction with Smad2, M10 reduces TGFβ-induced phosphorylation of Smad2 in skin and lung fibroblasts. Without being bound by a particular theory, as Smad2 phosphorylation is essential for TGFβ-regulated synthesis of collagen (Ishida et al., J Invest Dermatol. 2006, 126:1733-1744), inhibition of Smad2 phosphorylation might be one mechanism by which M10 exerts its antifibrotic effects.

Pulmonary fibrosis is a severe complication and a major cause of mortality in patients with scleroderma (Bogatkevich, Rheumatol Curr Res. 2012, S1:e001; Fan et al., Curr Opin Rheumatol. 2014, 26:630-636). The antifibrotic effects of M10 in vivo were explored using a model of pulmonary fibrosis using a single intratracheal administration of bleomycin in mice. Treatment with M10 by intraperitoneal injection markedly improved bleomycin-induced fibrosis. Therefore, without being bound to a particular theory, it is believed that M10 peptide may have potential for use in the treatment of scleroderma-associated ILD and other forms of pulmonary fibrosis, for example, idiopathic pulmonary fibrosis.

There is a great need for more effective therapy for SSc-ILD and other fibrosing diseases. In fact, fibrotic diseases account for up to 45% of deaths in the developed world, yet there are no approved antifibrotic therapies (Wynn, J Pathol. 2008, 214:199-210). Peptide drugs have been successfully used for many diseases for over 40 years (Vlieghe et al., Drug Discov Today, 2010, 15:40-56). Peptides offer certain advantages as drugs including high biological activity, high specificity, and low toxicity. As demonstrated herein, the in vitro and in vivo antifibrotic effects of M10 are very promising and further development may lead to more effective therapy for patients who suffer from SSc and other fibrosing diseases.

The materials and methods are now described.

M10 and 10 amino acid scrambled peptides were obtained from GenScript (Piscataway, N.J.), red fluorescent 5,6-carboxytetramethyl-rhodamine, succinimidyl ester (5,6-TAMRA)-conjugated M10 was purchased from BioSynthesis (Lewisville, Tex.). Anti-type I collagen antibody was from Southern Biotechnology (Birmingham, Ala.), anti-Met (C12) antibody was from Santa Cruz Biotechnology (Santa Cruz, Calif.), anti-Smad2 and anti-phospho-Smad2 was from Cell Signaling Technology (Danvers, Mass.), anti-β-actin was from Sigma (St. Louis, Mo.). Alexa Fluor 647® conjugated goat anti-rabbit secondary antibody, Alexa Fluor 488® Phalloidin, and ProLong® Gold anti-fade mountant with DAPI were obtained from Life Technologies (Grand Island, N.Y.). Recombinant human Smad2 (NM 005901) with C-terminal MYC/DDK tag, Smad4 (NM 005359) with C-terminal MYC/DDK tag, and anti-DDK antibody were purchased from OriGene Technologies (Rockville, Md.), TGFβ was from R&D Systems (Minneapolis, Minn.), bleomycin sulfate was from Hospira Inc. (Lake Forest, Ill.).

Cell Culture

Lung tissues were collected postmortem from three SSc patients who fulfilled the 2013 ACR/EULAR classification criteria for SSc (Van den Hoogen, et al., Arthritis Rheum, 2013, 65:2737-47) and had evidence of lung involvement according to guidelines of the IRB of the Medical University of South Carolina (MUSC). The diagnosis of SSc-ILD was confirmed by histological examination of postmortem lung tissue. Lung fibroblasts were isolated from scleroderma lung tissue and from normal controls as previously described (Bogatkevich, et al., J Biol Chem, 2001, 276, 45184-92) and used between second and fourth passages in all experiments. Human fetal lung fibroblasts MRC5 were purchased from Sigma (St. Louis, Mo.). Skin fibroblasts were isolated from 3-5 mm skin biopsies obtained from the involved forearm skin of scleroderma patients and from age-, sex-, and race-matched healthy adult donors according to guidelines of the MUSC IRB. Skin was cleared of fat and hair, diced (0.5×0.5 mm pieces), and cultured in Dulbecco's modified Eagle's medium (DMEM; Gibco, Grand Island, N.Y.) supplemented with 20% fetal bovine serum (FBS), 2 mM 1-glutamine, gentamicin sulfate (50 µg/ml), and amphotericin B (5 µg/ml) at 37° C. in 5% CO2. Medium was changed every five days to remove dead and non-attached cells until fibroblasts reached confluence. Monolayer cultures were maintained in the 10% FBS DMEM.

Immunofluorescent Studies

Cells were cultured to subconfluence on glass slides, serum-starved overnight, and incubated with M10 or 5,6-TAMRA-M10 with and without TGFβ for 24 hours. Cells were fixed with 4% formaldehyde and blocked with PBS containing 5% BSA, 0.1% Triton, and 0.0004% Sodium Azide. A part of the slides were immunostained with anti-MET C12 antibody or with anti-Smad2 antibody followed by Alexa Fluor 647® conjugated goat anti-rabbit secondary antibody. Next, slides were washed with PBS and incubated with Alexa Fluor 488® phalloidin for 30 minutes (dilution in PBS 1:50). The labeled slide was mounted with ProLong Gold anti-fade reagent with DAPI and visualized under Olympus FV10i laser scanning confocal or Zeiss Axio Imager M2 microscope system.

Preparation of Cell Extracts, Immunoprecipitation, and Immunoblotting

Cells were collected and analyzed by immunoblotting as previously described (Bogatkevich et al., J Biol Chem. 2001, 276:45184-45192; Bogatkevich et al., Arthritis Rheum. 2007, 56:3468-3477). The phosphorylation of Smad2 was analyzed by Western blot using anti-phospho-Smad2 antibody in accordance with the manufacturer's instructions (Cell Signaling Technology). Briefly, lung and skin fibroblasts were cultured on 6-well plates ($2\times10^6$ cells/well) to 90% confluence, synchronized with serum-free DMEM for 24 hours, and then pretreated for 40 minutes with or without M10. Next, cells were incubated with or without TGFβ (5 ng/ml) for 20 minutes, rapidly washed with ice-cold PBS and collected in 1×SDS sample buffer (100 µl/well). Twenty µl of sample was separated on 4-20% SDS polyacrylamide gels and immunoblotted with anti-phospho-Smad2 antibody. Total amount of Smad2 was evaluated by re-blotting with anti-Smad2 polyclonal antibody.

For immunoprecipitation assay, scleroderma skin and lung fibroblasts were grown to confluence on 100 mm plates, kept in serum-free DMEM overnight, incubated with M10 for 24 h, washed with ice cold PBS, and collected with 1 ml of ice-cold solubilization buffer consisting of 10 mM Tris-HCl, pH 7.4, 10 mM EDTA, 150 mM NaCl, 1% Nonidet P-40, 0.5% deoxycholate, 0.1% SDS. Samples were rotated for 3 h and then cleared by microcentrifugation at 4° C. Next, anti-C12 antibody (1 µg) was added, and the samples were rotated for 90 minutes at 4° C. Immune complexes were isolated on protein G-sepharose beads (Amersham Pharmacia Biotech, Piscataway, N.J.), washed with buffer containing 10 mM Tris-HCl, pH 7.4 and 10 mM EDTA, resolved by gel electrophoresis, and immunoblotted with anti-Smad2 antibody.

Protein Interaction Assay

DDK-tagged recombinant Smad2 and Smad4 were incubated with M10 (1 µg each) in a total volume of 500 µl of Buffer A (20 mM Tris-HCl, pH 7.5, 0.6 mM EDTA, 70 mM NaCl, 0.01% Thesit) at 4° C. for 40 minutes with gentle rotation. C-12 antibody (1 µg) was added, and incubation was continued for another 30 minutes followed by adding 50 µl of protein G-sepharose slurry for an additional 20 minutes. The resin was washed three times with buffer A; the retained proteins were solubilized in Laemmli sample buffer and subjected to immunoblotting with anti-DDK monoclonal antibody.

Bleomycin-Induced Model of Lung Fibrosis

Mice (n=6), C57BL/6 male were used in this study. Mice were maintained in animal quarters specially designated for pathogen-free mice and were provided with food and water ad libitum. Lung injury was induced by intratracheal instillation of bleomycin (2 U/kg in saline) under isoflurane anesthesia. Control mice received same volume of saline. M10 (10 mg/kg) was administrated intraperitoneal every 48 hours. Control mice received 10 mg/kg scrambled peptide. Animals were sacrificed in 3 weeks, and lungs were harvested and processed for tissue staining. All experimental procedures were performed according to guidelines of the Institutional Animal Care and Use Committee of the Medical University of South Carolina.

Lung Fixation and Histological Examinations

Sacrificed mice were subjected to midline thoracotomy. The trachea was cannulated, and the lungs were fixed by instillation of buffered formalin (2%) for 24 hours followed by perfusion with 70% ethanol for another 24 hours before routine processing and paraffin embedding as previously described (Bogatkevich, et al., Arthritis Rheum, 2011, 63(5): 1416-25).

To evaluate the stages of lung fibrosis, multiple sections from each lung were stained with Hematoxylin and eosin (H & E staining) or with trichrome staining for collagen and other extracellular matrix proteins. Fibrosis quantification was performed by using 0 (normal) to 8 (total fibrosis) Ashcroft scale (Ashcroft, et al., J Clin Pathol, 1988, 41:467-470). Morphological changes such as the thickness of alveolar septa, accumulation of vascular component and connective tissue, infiltration of inflammatory cells were analyzed. For histological evaluation each specimens were divided in 10 non-overlapping fields and scored independently. To avoid bias, three individuals in blinded fashion evaluated all histological specimens. The mean value from the individual score is presented as the fibrotic score.

Statistical Analysis

Statistical analyses were performed with KaleidaGraph 4.0 (Synergy Software, Reading, Pa.). All data were analyzed using ANOVA with post-hoc testing.

The results were considered significant if $p<0.05$.

The results of the experiments are now described

M10 Generation and Intracellular Localization

Figures 8A, 8B, 8C, 8D:
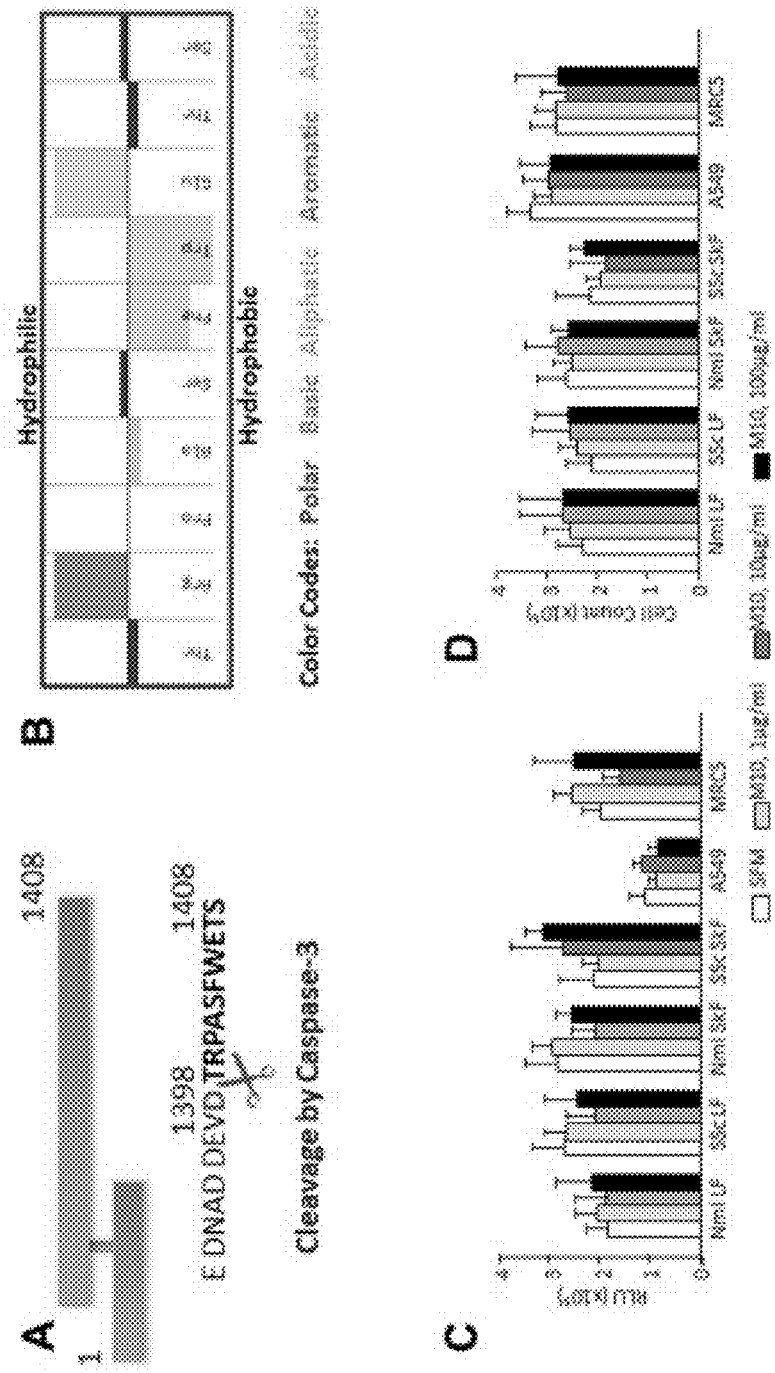
FIG. 8A depicts the position of M10 on the MET receptor tyrosine kinase. The cleavage site of caspase 3 is indicated by scissors.
FIG. 8B depicts a jydropathy plot of M10, prepared by the Hopp-Woods hydrophilicity scale. Hydrophilic residues are presented as upward bars, and hydrophobic residues are presented as downward bars.
FIG. 8C depicts M10 does not affect cell viability measured by the ATP-dependent assay.
FIG. 8D depicts similar findings as FIG. 8C using trypan blue cell counting. RLU, relative light unit; SSc, systemic sclerosis.

M10 is a peptide, comprising the last 10 amino acids (TRPASFWETS; SEQ ID NO: 1) of the HGF receptor, MET (FIG. 8A). M10 is generated from MET's intracellular cytoplasmic tail upon cleavage by caspase-3. M10 has the chemical formula $C_{53}H_{76}N_{14}O_{17}$, a molecular weight of 1181.27 g/mol, and an isoelectric point at pH 6.97. Synthetic M10, obtained from GenScript (Piscataway, N.J.) at pharmaceutical grade purity, is an off-white lyophilized powder that is well soluble in water. The hydropathy for each standard amino acid in the M10 peptide is shown in FIG. 8B.

Figures 9A, 9B, 9C, 9D, 9E, 9F, 9G, 9H, 9I:
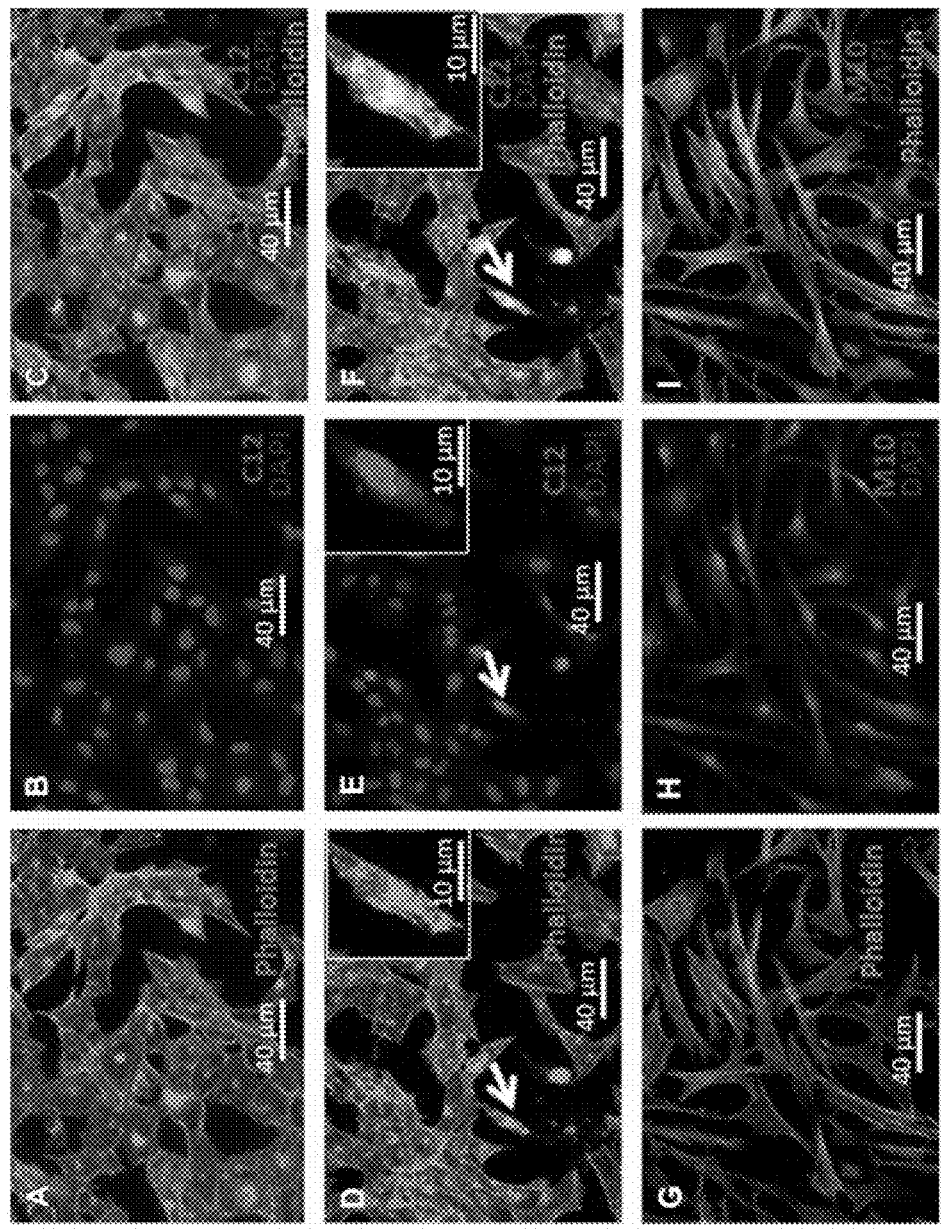
FIGS. 9A through 9F depict lung fibroblasts were seeded on 4-chamber slides, serum starved for 24 hours followed by incubation for 24 hours with M10 or scrambled peptide (10 µg/mL). Cells were fixed with 4% formaldehyde and stained with anti-Met (C12) antibody.
FIGS. 9G through 9I depict fibroblasts incubated with TAMRA-conjugated M10 (G-I). After labeling, slides were mounted by Gold antifade reagent with Phalloidin and DAPI and visualized using a Leica DMI4000B fluorescence microscope equipped with Hamamatsu Camera Controller ORCA-ER. White arrows in FIGS. 9D through 9F indicate C12-positively stained cells, 4×-magnified in the upper right-hand corner.

M10 contains at its N-terminus the uncharged amino acid proline (P) directly after a cationic amino acid arginine (R), which favors the transport of the peptide through membranes (Fonseca, et al., Adv Drug Deliv Rev, 2009, 61:953-64). To follow the localization of M10 inside of cells, an anti-Met C12 antibody that is generated against the last 12 amino acids of MET and recognizes M10, but not a scrambled peptide, was used as a control. Additionally, M10 was used directly conjugated with the red fluorescent marker 5,6-TAMRA at the N-terminus. Following 24 hours of exposure, M10 and 5,6-TAMRA-M10 are localized in the cytoplasm and nuclei of lung and skin fibroblasts (FIG. 9).

Effects of M10 on Collagen in Scleroderma and Normal Lung and Skin Fibroblasts

Figures 10A, 10B, 10C, 10D:
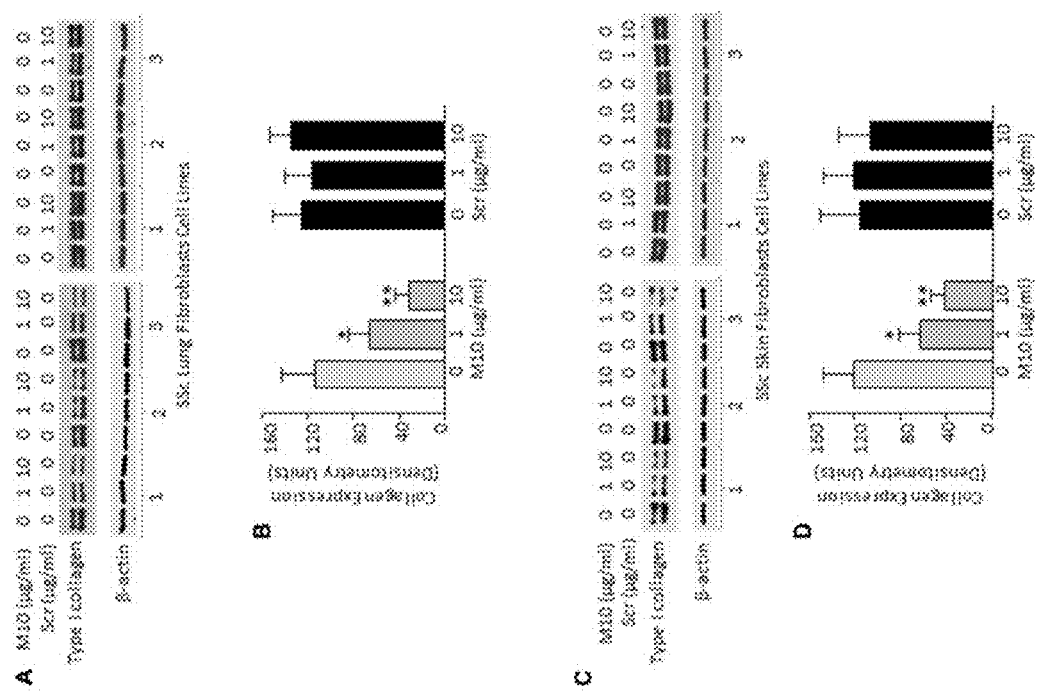
FIG. 10A through FIG. 10D, depicts a concentration-dependent effect of M10 on the expression of collagen type I in scleroderma lung and skin fibroblasts.

To determine whether M10 affects collagen expression in scleroderma fibroblasts, skin and lung fibroblasts isolated from six SSc patients was incubated with M10 and performed Western blot analysis using anti-type I collagen antibody. As expected, SSc lung and skin fibroblasts demonstrated high levels of collagen expression at baseline. M10, added to the cells in a dose of 1 μg/ml and 10 μg/ml for 24 hours, effectively reduced collagen expression in a dose dependent manner in all SSc lung (FIG. 10A and FIG. 10B) and skin fibroblast cell lines (FIG. 10C and FIG. 10D). A scrambled peptide did not have any effect on collagen in any of the studied cell lines.

Figures 11A, 11B:
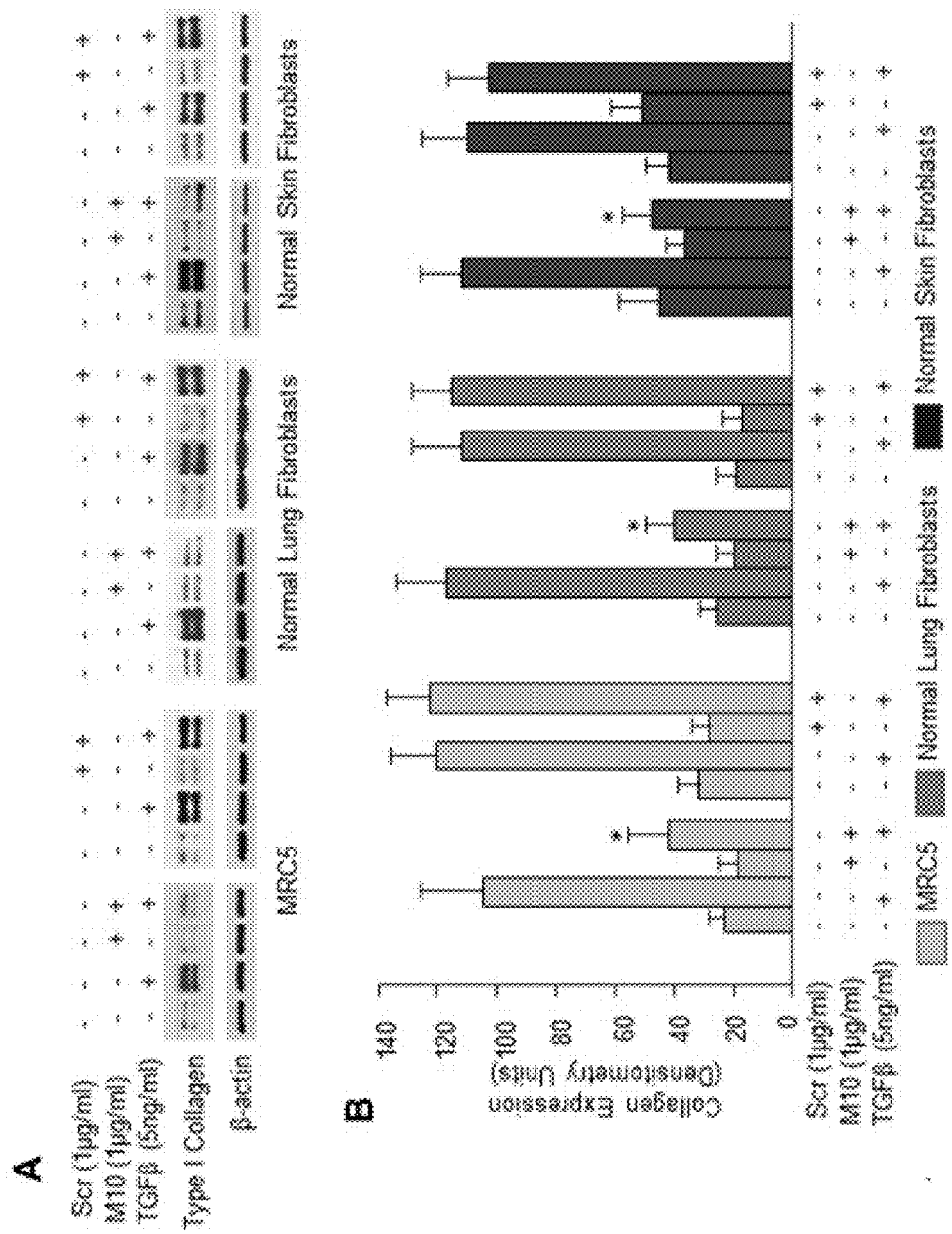
FIG. 11A and FIG. 11B, depicts the effect of M10 on TGFβ-induced collagen type 1.

Next, the effect of M10 on the levels of type I collagen in normal fibroblasts was investigated. Since normal fibroblasts contain less collagen as compared with scleroderma fibroblasts, TGFβ was used to stimulate collagen production. M10 at a concentration of 1 μg/ml, but not a scrambled peptide, significantly reduced levels of TGFβ-induced collagen in fetal lung fibroblasts (MRC5 immortal cell line) and in primary normal lung and skin fibroblasts (($p<0.01$), FIG. 11). Importantly, M10 had no effect on the basal levels of collagen in any of studied normal fibroblast cell lines.

Investigation of M10 Antifibrotic Mechanism

Figures 12A, 12B, 12C:
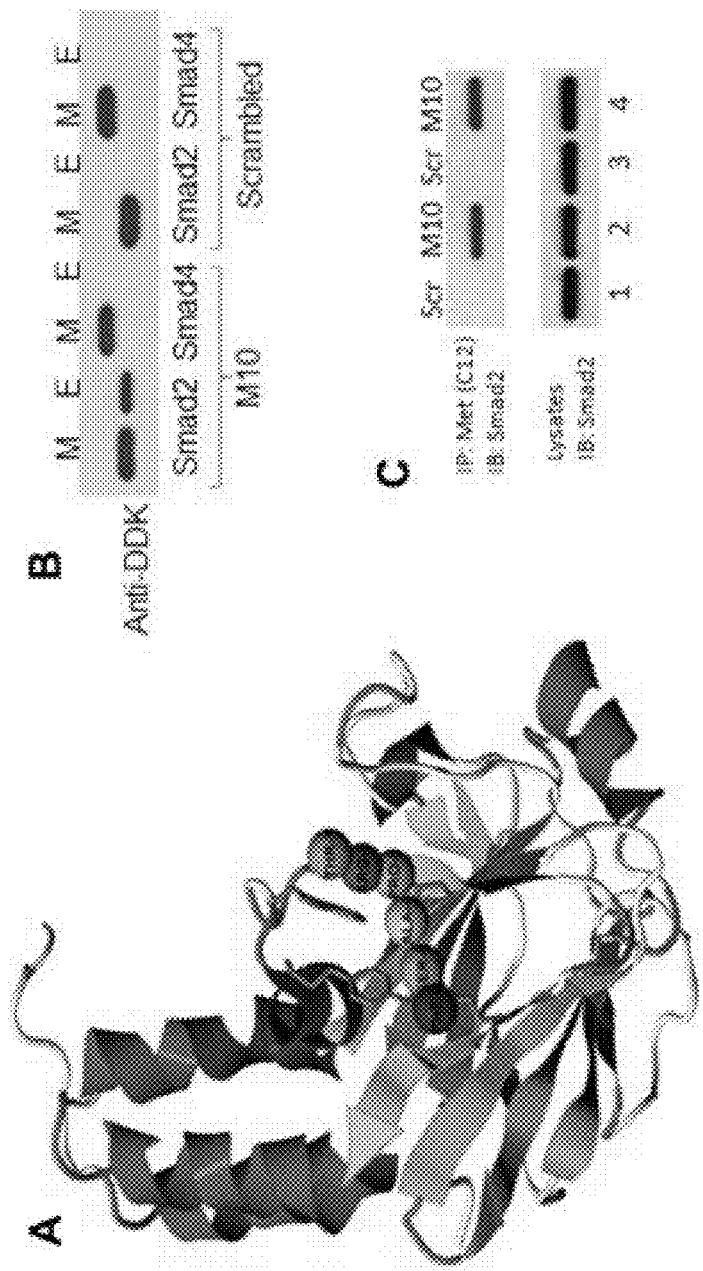
FIG. 12A through FIG. 12C, depicts M10 and Smad2 interaction.

Since M10 reduces TGFβ-stimulated collagen, a computational modulation approach to explore possible interference of M10 with TGFβ signaling pathways was employed. Using computational modeling available from PepSite: prediction of peptide-binding sites from protein surfaces (Trabuco et al., Nucleic Acids Res. 2012, 40:W423-W427), a statistically significant ($p<0.02$) potential interaction of M10 with the Mad Homology (MH)2 domain of Smad2 (FIG. 12A) was found. To confirm the predicted M10/Smad2 interaction, a set of peptide-protein interaction experiments using synthetic M10 and recombinant human Smad2 tagged with DDK was performed. As negative controls in these experiments, M10 incubated with DDK-tagged Smad4 and scrambled peptide incubated with DDK-tagged Smad2 was used. As a positive control for anti-DDK antibody, the gel was loaded with 5 μl-aliquots of a buffer containing DDK-tagged recombinant Smad2 or Smad4 proteins. M10 interactions with Smad2, but not with Smad4, and that scrambled peptide does not interact with Smad2 or with Smad4 (FIG. 12B) was observed.

Next, co-immunoprecipitation experiments to test whether M10 and Smad2 actually interact in lung and skin fibroblasts were performed. For these experiments, scleroderma lung and skin primary fibroblasts characterized by high expression of endogenous Smad2 were used. An interaction of Smad2 with M10 in both lung and skin fibroblasts that were treated with M10, but not in cells treated with a scrambled peptide (FIG. 12C) was observed.

Figures 13A, 13B:
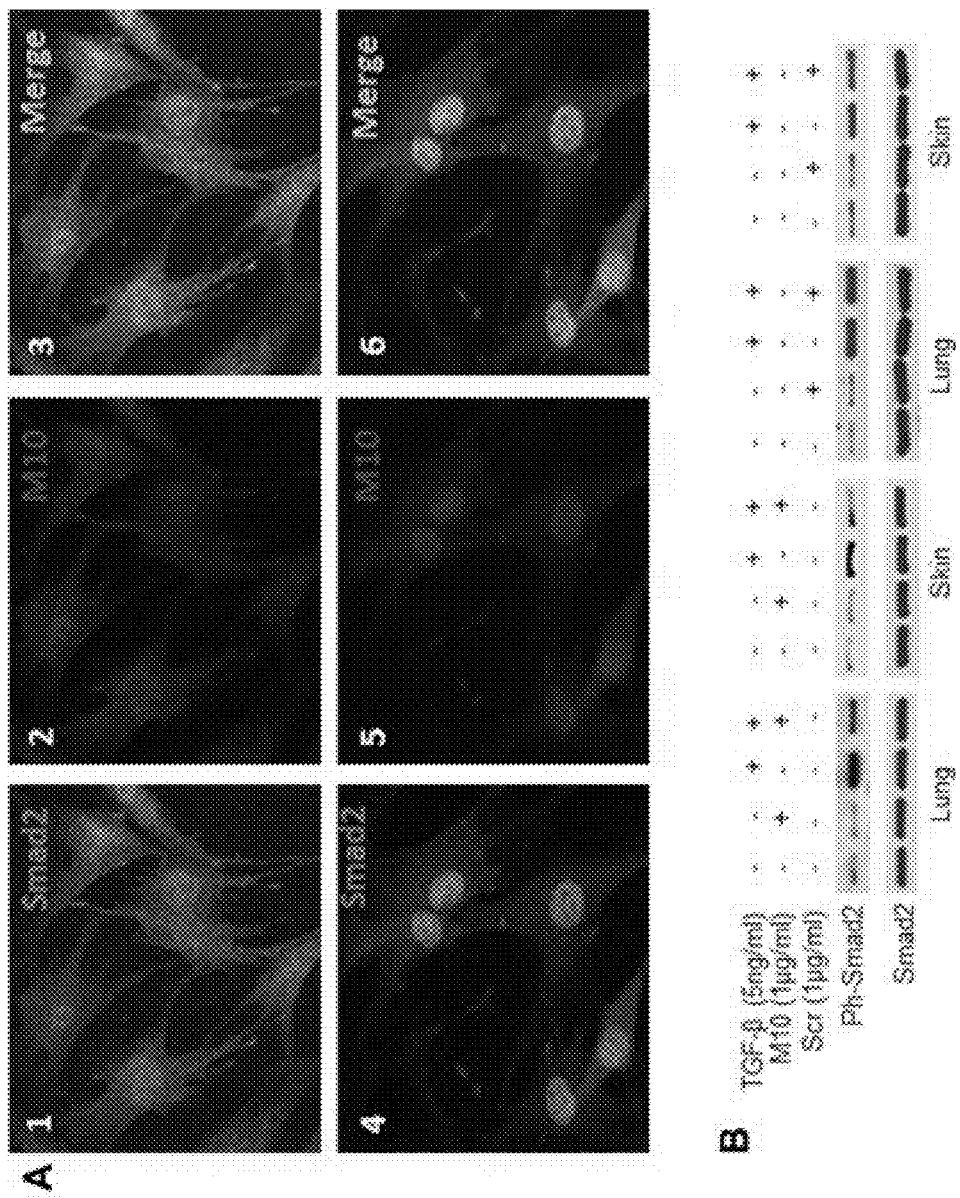
FIG. 13A and FIG. 13B, depicts M10 colocalizes with Smad2 and inhibits TGFβ-induced Smad2 phosphorylation.
Figures 14A, 14B, 14C:
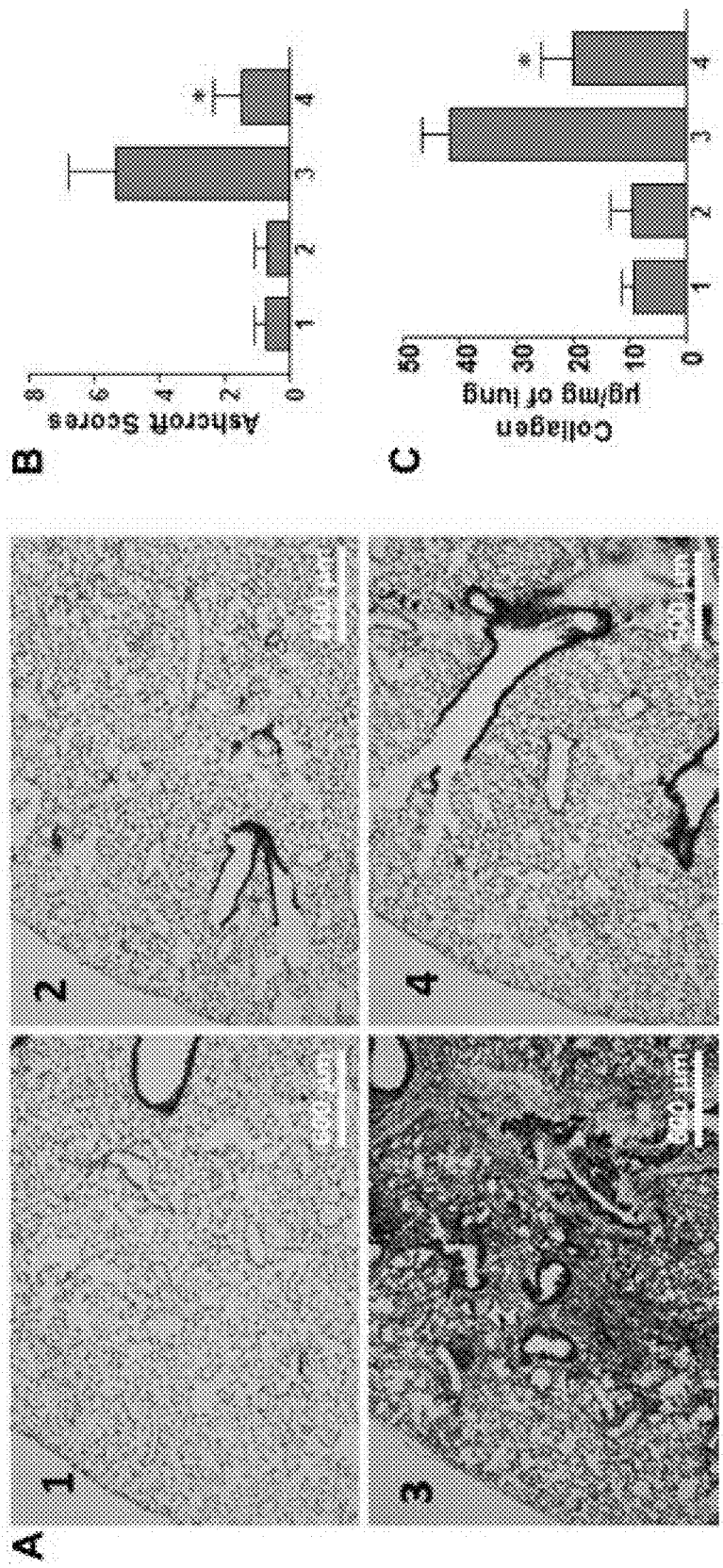
FIG. 14A through FIG. 14C, depicts the effect of M10 on bleomycin-induced pulmonary fibrosis.

To further investigate the interaction of M10 with Smad2, co-localization of M10 and Smad2 in primary lung fibroblasts in the presence and absence of TGFβ was studied. M10 and Smad2 co-localize with or without TGFβ treatment. Interestingly, without TGFβ treatment M10 and Smad2 are distributed in the cytoplasm and nuclei of these cells. However, after TGFβ treatment M10 and Smad2 accumulate and co-localize mostly in the nuclei of these cells (FIG. 13A).

TGFβ leads to the phosphorylation of Smad2. To determine whether M10 interferes with TGFβ-induced Smad2 phosphorylation, TGFβ-induced Smad2 phosphorylation in the presence and absence of M10 in lung and skin fibroblasts was studied. Within 20 minutes of TGFβ stimulation, Smad2 phosphorylation was significantly increased as compared to unstimulated cells. M10, at a concentration of 1 μg/ml, decreased TGFβ-induced Smad2 phosphorylation but did not affect the basal level of phospho-Smad2 or total Smad2 (FIG. 13B).

Antifibrotic Effects of M10 in a Bleomycin Murine Model of Pulmonary Fibrosis

In control mice that received saline and scrambled peptide or saline and M10, lung histology was characterized by alveolar structures composed of normal septa, vascular components, and connective tissue. Lung tissue isolated from bleomycin-treated mice demonstrated thickening of the alveolar walls and multiple focal fibrotic lesions with excessive amounts of ECM protein (FIG. 14A-D). By contrast, decreased thickness of alveolar septa and reduced accumulation of ECM proteins were noted in mice treated with M10.

The overall level of fibrotic changes was quantitatively assessed based on the Ashcroft scoring system (Ashcroft, et al., J Clin Pathol, 1988, 41:467-470). The Ashcroft fibrosis score in mice treated with bleomycin and scrambled peptide was 8.2-fold higher than control (saline-treated) mice (5.63±1.72 and 0.69±0.35, respectively; $p<0.05$). The Ashcroft fibrosis score in bleomycin treated mice treated with M10 was reduced to 1.67±1.01, reflecting a pronounced antifibrotic effect of M10 ($p<0.05$) (FIG. 14E).

Example 3. Investigation of Effect of 1403 and 1404 Peptides on Alveolar Epithelial Cell Apoptosis Although the pathogenesis of pulmonary fibrosis is unclear, a large body of evidence indicates that increased apoptosis of alveolar epithelial cells (AEC) and activation of LF are fundamental processes in this disease (Zoz, et al., Am J Med Sci, 2011, 341(6):435-8; Hardie, et al., Am J Pathol, 2009, 175(1):3-16 and Barkauskas, et al., Am J Physiol Cell Physiol, 2014, 306(11):C987-96). M10 demonstrates robust antifibrotic effects in LF; however, M10 does not affect apoptosis of AEC. By adding the caspase-3 cleavage sites DEVD to M10, a peptide 1404 comprising the sequence DEVDTRPAS (SEQ ID NO: 2), was generated with the ability to inhibit pro-apoptotic caspase-3 in AEC, thereby protecting these cells from apoptosis while retaining the antifibrotic properties of M10. The commercially available caspase 3 inhibitor Z-DEVD-FMK (benzyloxycarbonyl-Asp(OMe)-Glu(OMe)-Val-Asp(OMe)-fluoromethyl ketone) contains benzyloxycarbonyl right in front of DEVD motif. To mimic this inhibitor, another aspartic acid (D) was added in front of DEVD such creating the peptide 1403 comprising the sequence DDEVDTRPAS (SEQ ID NO: 3).

Figure 15:
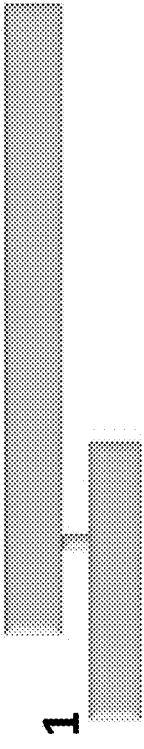
FIG. 15 depicts the MET-derived peptides. SEQ ID NO: 5 provides the sequence of the C-Terminus of MET.
Figure 16A:
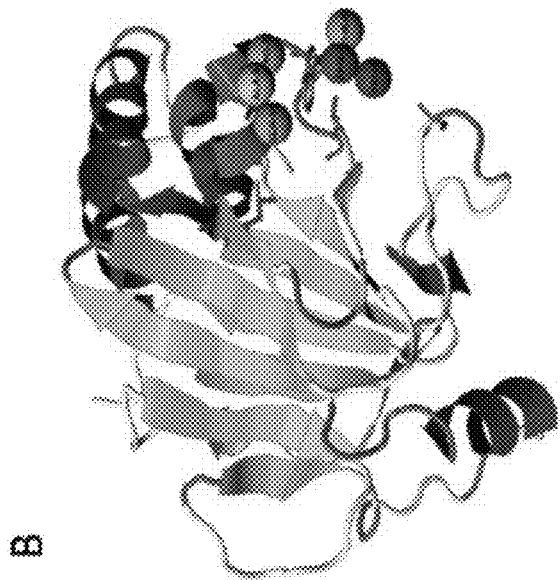
FIG. 16A and FIG. 16B, depicts TRPAS (SEQ ID NO: 4) amino acids of 1403 and 1404 peptides in complex with Smad2 and Smurf2 proteins. The interactive visualization of statistically significant (p<0.01) binding of TRPAS (SEQ ID NO: 4) amino acids of 1404 peptide with 2KXQ domain of Smurf2 (FIG. 16A) and 1 U7V domain of Smad2 (FIG. 16B) are presented.
Figure 16B:

Using advanced computational molecular modeling based on the peptide-binding sites from protein surfaces (Trabuco. Et al., Nucleic Acids Res, 2012, 40(Web Server issue): W423-7), it was determined that TRPAS (SEQ ID NO: 4) amino acids of M10, 1403, and 1404 peptides (FIG. 15) are responsible for peptide-protein interactions with Smad2 and Smurf2 (FIG. 16).

Figures 17A, 17B:
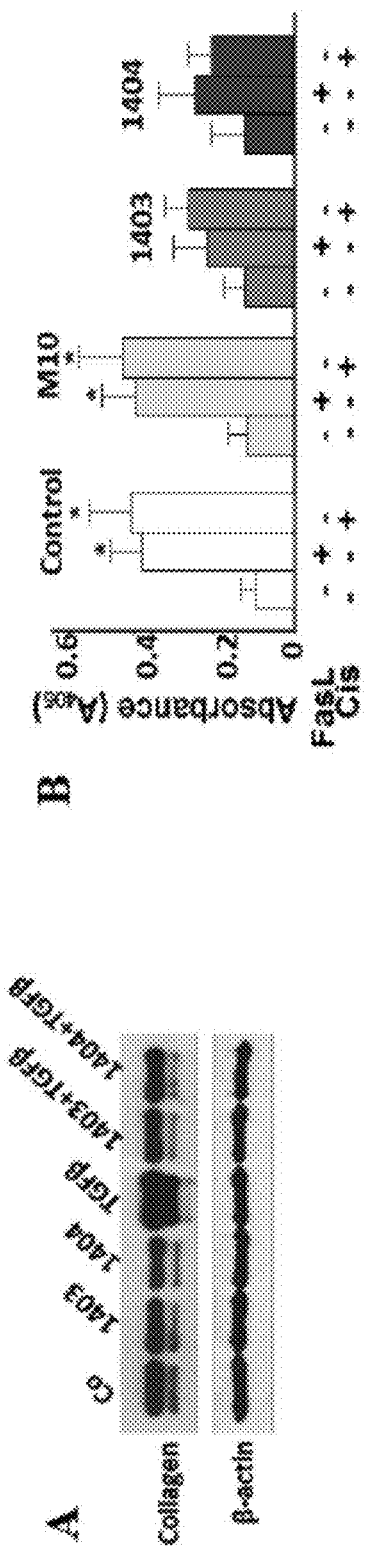
FIG. 17A and FIG. 17B, depicts 1403 and 1404 peptides demonstrate antifibrotic effects in lung fibroblasts (LF) and anti-apoptotic effects in alveolar epithelial cells (AEC).

To investigate whether 1403 and 1404 peptides affect the levels of type I collagen in LF, TGFβ-stimulated fetal lung fibroblasts (MRC5 immortal cell line) were studied. It was observed that 1403 or 1404 peptides at a concentration of 1 μg/ml, but not a scrambled peptide, significantly reduced levels of TGFβ-induced collagen in LF (FIG. 17A). Importantly, M10 had no effect on the basal levels of collagen in LF.

To investigate if the 1403 and 1404 peptides have anti-apoptotic effects in AEC, apoptosis of AEC was induced with FasL and cisplatin and measured caspase 3 activity in cell lysates. Incubation of AEC for 24 hours with either FasL or cisplatin resulted in apoptosis reflected by an increase in the level of active caspase 3. Treatment of AEC with either 1403 or 1404 peptides significantly reduced apoptosis decreasing FasL- and cisplatin-induced caspase (p<0.01). In contrast, AEC treated with scrambled peptide were not protected from FasL- and cisplatin-induced apoptosis (FIG. 17B).

Example 4. Investigation of Effect of M5 Peptide on Collagen

Figure 18:
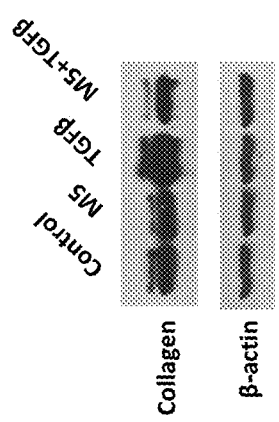
FIG. 18 depicts M5 peptide inhibits collagen in TGFβ-stimulated lung fibroblasts. Cells were incubated with and without TGFβ (5 ng/ml) and M5 peptide (1 µg/ml) for 24 h and analyzed by immunoblotting using anti-collagen type I antibody. Beta-actin was used as a loading control.

The TRPAS (SEQ ID NO: 4) amino acids of M10, 1403, and 1404 peptides (FIG. 15) are responsible for peptide-protein interactions with Smad2 and Smurf2 (FIG. 16). A peptide containing just the M5 sequence (TRPAS (SEQ ID NO: 4)) was generated and was tested for its effect on collagen. FIG. 18 shows that fibroblasts stimulated with TGFβ and incubated with M5 peptide (1 μg/ml) for 24 h had a reduced level of collagen as compared to fibroblasts stimulated with TGFβ. The data indicate that the M5 peptide functions similarly to the M10, 1403 and 1404 peptides to reduce collagen.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a subject with fibrosis, the method comprising administering to the subject a therapeutically effective amount of a pharmaceutical composition comprising an isolated peptide comprising an amino acid sequence selected from the group consisting of SEQ ID NO:1, SEQ ID NO: 2, SEQ ID NO:3, SEQ ID NO:4, SEQ ID NO:5, SEQ ID NO:6 and SEQ ID NO:7, thereby treating the subject with fibrosis.

2. The method of claim 1, wherein the subject has a fibrosis of the skin.

3. The method of claim 1, wherein the subject has scleroderma.

4. The method of claim 1, wherein the subject has idiopathic pulmonary fibrosis.

5. The method of claim 1, wherein the subject has scleroderma associated interstitial lung disease.

6. The method of claim 1, wherein the fibrosis is selected from the group consisting of kidney fibrosis, liver fibrosis, cardiac fibrosis, pulmonary fibrosis, restenosis-related vascular fibrosis, spleen fibrosis, age-related fibrosis, skin fibrosis, and post-transplantation fibrosis.

7. The method of claim 1, further comprising administering to the subject a therapeutically effective amount of a therapeutic agent.

8. The method of claim 7, wherein the therapeutic agent is selected from the group consisting of an anti-inflammatory agent, an immunosuppressive agent, an anti-diabetic agent, digoxin, a vasodilator, an angiotensin II converting enzyme (ACE) inhibitors, an angiotensin II receptor blockers (ARB), a calcium channel blocker, an isosorbide dinitrate, a hydralazine, a nitrate, a hydralazine, a beta-blocker, a natriuretic peptides, a heparinoid, and a connective tissue growth factor inhibitor.

9. The method of claim 1, wherein the isolated peptide comprises the amino acid sequence of SEQ ID NO: 1.

10. The method of claim 1, wherein the isolated peptide comprises the amino acid sequence of SEQ ID NO:2.

11. The method of claim 1, wherein the isolated peptide comprises the amino acid sequence of SEQ ID NO:3.

12. The method of claim 1, wherein the isolated peptide comprises the amino acid sequence of SEQ ID NO: 4.

13. The method of claim 1, wherein the isolated peptide comprises the amino acid sequence of SEQ ID NO:5.

14. The method of claim 1, wherein the isolated peptide comprises the amino acid sequence of SEQ ID NO: 6.

15. The method of claim 1, wherein the isolated peptide comprises the amino acid sequence of SEQ ID NO: 7.

* * * * *